United States Patent
Asakura et al.

(12)

(10) Patent No.: US 6,512,020 B1
(45) Date of Patent: Jan. 28, 2003

(54) OXIME DERIVATIVES AND THE USE THEREOF AS LATENT ACIDS

(75) Inventors: Toshikage Asakura, Minoo (JP); Hitoshi Yamato, Takarazuka (JP); Masaki Ohwa, Kobe (JP); Jean-Luc Birbaum, Binningen (CH); Kurt Dietliker, Allschwil (CH); Junichi Tanabe, Takarazuka (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 115 days.

(21) Appl. No.: 09/820,115

(22) Filed: Mar. 28, 2001

Related U.S. Application Data

(62) Division of application No. 09/533,952, filed on Mar. 23, 2000, now Pat. No. 6,261,738.

(30) Foreign Application Priority Data

Mar. 31, 1999 (EP) .............................. 99810273
Apr. 7, 1999 (EP) .............................. 99810287
Aug. 30, 1999 (EP) .............................. 99810779

(51) Int. Cl.$^7$ .............................. C08J 3/28; G03C 1/72; G03F 7/028; C07C 131/00
(52) U.S. Cl. .............................. 522/57; 522/59; 522/65; 522/26; 522/27; 522/28; 522/126; 430/270.1; 430/281.1; 427/508; 427/510; 427/511; 427/517; 564/253; 564/254; 564/256; 568/28; 568/30; 570/123
(58) Field of Search .............................. 430/270.1, 281.1; 522/126, 28, 26, 27, 57, 59, 65; 427/508, 510, 511, 517; 564/253, 256, 254; 568/28, 30; 570/123

(56) References Cited

U.S. PATENT DOCUMENTS

| | | | |
|---|---|---|---|
| 4,329,488 A | * 5/1982 | Frater et al. | 504/316 |
| 4,540,598 A | 9/1985 | Berner et al. | 427/54.1 |
| 4,736,055 A | 4/1988 | Dietliker et al. | 560/13 |
| 5,354,883 A | 10/1994 | Isak et al. | 560/35 |
| 5,627,011 A | 5/1997 | Münzel et al. | 430/270.1 |
| 5,714,625 A | 2/1998 | Hada et al. | 558/437 |
| 5,759,740 A | 6/1998 | Münzel et al. | 430/270.1 |
| 5,976,760 A | * 11/1999 | Oomori et al. | 430/270.1 |
| 6,004,724 A | 12/1999 | Yamato et al. | 430/281.1 |
| 6,017,675 A | 1/2000 | Dietliker et al. | 430/270.1 |
| 6,042,988 A | * 3/2000 | Sato et al. | 430/270.1 |
| 2002/0051936 A1 | * 5/2002 | Harada et al. | 430/270.1 |

FOREIGN PATENT DOCUMENTS

| | | |
|---|---|---|
| EP | 241423 | 4/1987 |
| EP | 0332158 | 9/1989 |
| EP | 0435687 | 7/1991 |
| EP | 0768572 | 4/1997 |
| GB | 2306958 | 5/1997 |
| WO | 99/01429 | 1/1999 |

OTHER PUBLICATIONS

Chem. Abstr. 97:144503; Jia Yunyi et al., Beckmann rearrangement of fluoroketoximes.
Chem. Abstr. 78:97752; Zeifman Yu et al., Derivatives of hexafluoroacetone oxime.
Synthesis, May 1995, John B.C. Findlay et al., p. 553.
XP–002113444, Bioconjugate Chemistry, (1991), vol. 2, No. 5, pp. 337–341.
XP–002113445, Journal of American Chemical Society, vol. 115, (1993), pp. 3458–3474.

* cited by examiner

*Primary Examiner*—Susan W. Berman
(74) *Attorney, Agent, or Firm*—David R. Crichton

(57) ABSTRACT

Compounds of formula I, II and III, wherein

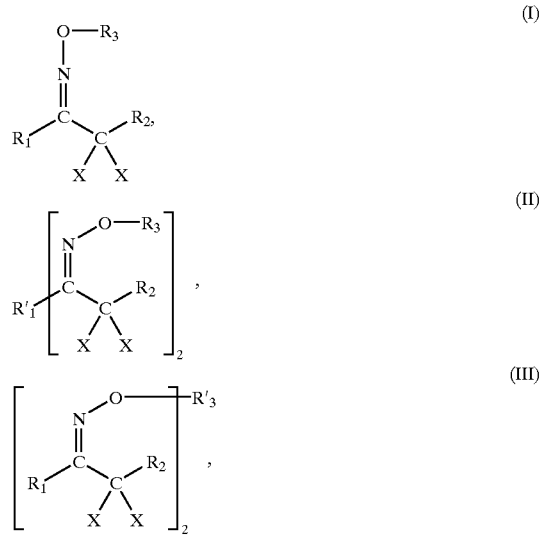

wherein $R_1$ is for example hydrogen, $C_1$–$C_{12}$alkyl, $C_3$–$C_{30}$cycloalkyl, $C_2$–$C_{12}$alkenyl, $C_4$–$C_8$cycloalkenyl, phenyl, which is unsubstituted or substituted, naphthyl, anthracyl or phenanthryl, unsubstituted or substituted, heteroaryl radical which is unsubstituted or substituted; wherein all radicals $R_1$ with the exception of hydrogen can additionally be substituted by a group having a —O—C-bond or a —O—Si-bond which cleaves upon the action of an acid; $R'_1$ is for example phenylene, naphthylene, diphenylene or oxydiphenylene, wherein these radicals are unsubstituted or substituted; $R_2$ is halogen or $C_1$–$C_{10}$haloalkyl; $R_3$ is for example $C_1$–$C_{18}$alkylsulfonyl, phenylsulfonyl, naphthylsulfonyl, anthracylsulfonyl or phenanthrylsulfonyl, wherein the groups are unsubstituted or substituted, or $R_3$ is e.g. $C_2$–$C_6$haloalkanoyl, or halobenzoyl, $R'_3$ is for example phenylenedisulfonyl, naphthylenedisulfonyl, diphenylenedisulfonyl, or oxydiphenylenedisulfonyl, wherein these radicals are unsubstituted or substituted, X is halogen; are especially suitable as photosensitive acid-donors in chemically amplified resist formulations.

5 Claims, No Drawings

OXIME DERIVATIVES AND THE USE THEREOF AS LATENT ACIDS

This application is a divisional of prior application Ser. No. 09/533,952 filed Mar. 23, 2000, now U.S. Pat. No. 6,261,738.

The invention relates to new oxime derivatives, chemically amplified photoresist compositions comprising said compounds and to the use of the compounds as latent acids, which can be activated by irradiation with actinic electromagnetic radiation and electron beams.

In U.S. Pat. No. 4,540,598 surface-coating compositions comprising photosensitive oxime sulfonate compounds, e.g. 4-chloro-α-trifluoroacetophenonoxime benzenesulfonate and customary acid-curable resins are disclosed. In U.S. Pat. No. 4,736,055 2,2,2-trifluoro-1-phenyl-ethanone oxime-O-(4-hydroxyphenylsulfonate) is described as a component for the preparation of polymers which can be used as resins in positive photoresists. In U.S. Pat. Nos. 5,627,011 and 5,759,740 the use of α-(4-toluene-sulfonyloxyimino)-4-methoxybenzyl cyanide and α-(4-toluene-sulfonyloxyimino)-3-thienylmethyl cyanide as latent acid catalysts in chemically amplified positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported. In U.S. Pat. No. 5,714,625 non aromatic α-(alkylsulfonyloxyimino)-1-cyclohexenylacetonitriles and α-(alkylsulfonyloxyimino)-1-cyclopentenylacetonitriles are disclosed. In EP 241423 oxime sulfonate compounds are employed in about 25% concentration as photolatent acid generators in non-chemically amplified positive resists. In Chemical Abstracts No. 97:144503, 78:97752, Synthesis (1995), 553, some fluoroketoxime sulfonate compounds are described as experimental products for synthetic studies.

In the art exists a need for reactive non-ionic latent acid donors that are thermally and chemically stable and that, after being activated by light, UV-radiation, X-ray irradiation or electron beams can be used as catalysts for a variety of acid-catalysed reactions, such as poly-condensation reactions, acid-catalysed depolymerisation reactions, acid-catalysed electro-philic substitution reactions or the acid-catalysed removal of protecting groups. A particular need exists for latent acid catalysts with high stability and good solubility in the field of chemically amplified photoresists.

Surprisingly, it has now been found that specific oxime derivatives, as described below, are especially suitable as catalysts for the aforementioned acid catalyzed reactions. The optical absorption spectra of the specific compounds of the invention are tunable over a wide range of the electromagnetic spectrum and particularly suitable for applications in the deep UV range. Furthermore, chemically amplified photoresist compositions comprising oxime derivatives of the present invention are thermally stable, even at high bake temperatures during processing and provide high photospeed.

The invention accordingly relates to a chemically amplified photoresist composition comprising (a) a compound which cures upon the action of an acid or a compound whose solubility is increased upon the action of an acid; and (b) as photosensitive acid donor, at least one compound of the formula I, II or III

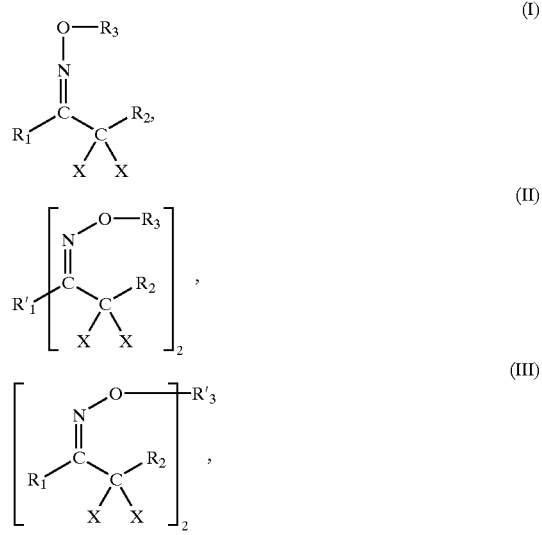

wherein
$R_1$ is hydrogen, unsubstituted $C_1$–$C_{12}$alkyl; $C_1$–$C_{12}$alkyl which is substituted by $C_3$–$C_{30}$cycloalkyl; or $R_1$ is $C_3$–$C_{30}$cycloalkyl, $C_1$–$C_8$haloalkyl, $C_2$–$C_{12}$alkenyl, $C_4$–$C_8$cycloalkenyl, $C_6$–$C_{12}$bicycloalkenyl, camphoryl; phenyl, which is unsubstituted or substituted by one or more of the radicals $C_1$–$C_{12}$alkyl, $C_1$–$C_4$haloalkyl, phenyl-$C_1$–$C_3$-alkyl, halogen, phenyl, $OR_4$, $NR_5R_6$, $SR_7$, $SOR_7$, and/or $SO_2R_7$, optionally the substituents $OR_4$, $SR_7$ and $NR_5R_6$ form 5- or 6-membered rings, via the radicals $R_4$, $R_5$, $R_6$ and/or $R_7$, with further substituents on the phenyl ring or with one of the carbon atoms of the phenyl ring;

or $R_1$ is naphthyl, anthracyl or phenanthryl, wherein the radicals naphthyl, anthracyl and phenanthryl are unsubstituted or substituted by $C_1$–$C_6$alkyl, phenyl, $OR_4$, $NR_5R_6$, $SR_7$, $SOR_7$, and/or $SO_2R_7$, optionally the substituents $OR_4$, $SR_7$ and $NR_5R_6$ form 5- or 6-membered rings, via the radicals $R_4$, $R_5$, $R_6$ and /or $R_7$ with further substituents on the naphthyl, anthracyl or phenanthryl ring or with one of the carbon atoms of the naphthyl, anthracyl or phenanthryl ring;

or $R_1$ is a heteroaryl radical which is unsubstituted or substituted by $C_1$–$C_6$alkyl, phenyl, $OR_4$, $NR_5R_6$, $SR_7$, $SOR_7$, and/or $SO_2R_7$, optionally the substituents $OR_4$, $SR_7$ and $NR_5R_6$ form 5- or 6-membered rings, via the radicals $R_4$, $R_5$, $R_6$ and/or $R_7$ with further substituents on the heteroaryl ring or with one of the carbon atoms of the heteroaryl ring;

wherein all radicals $R_1$ with the exception of hydrogen can additionally be substituted by a group having a —O—C-bond or a —O—Si-bond which cleaves upon the action of an acid;

$R'_1$ is phenylene, naphthylene,

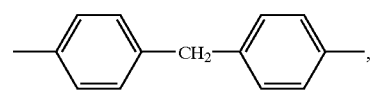

diphenylene or oxydiphenylene, wherein these radicals are unsubstituted or substituted by $C_1$–$C_{12}$alkyl; or $R'_1$ is $C_1$–$C_{12}$-alkylene or

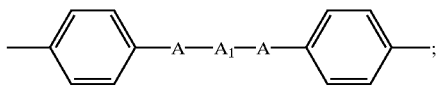

A is —O—, —S—, —NR₄—, —O(CO)—, —S(CO)—, —NR₄(CO)—, —SO—, —SO₂—, or —OSO₂—;

$A_1$ is $C_1$–$C_{12}$alkylene or $C_2$–$C_{12}$alkylene, which is interrupted by one or more —O—;

$R_2$ is halogen or $C_1$–$C_{10}$haloalkyl;

$R_3$ is $C_1$–$C_{18}$alkylsulfonyl, $C_1$–$C_{10}$haloalkylsulfonyl, camphorylsulfonyl, phenyl-$C_1$–$C_3$alkylsulfonyl, $C_3$–$C_{12}$cycloalkylsulfonyl, phenylsulfonyl, naphthylsulfonyl, anthracylsulfonyl or phenanthrylsulfonyl, wherein the groups cycloalkyl, phenyl, naphthyl, anthracyl and phenanthryl of the radicals $C_3$–$C_{12}$cycloalkylsulfonyl, phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_4$, $COOR_7$, $C_1$–$C_4$alkyl-(OC)O—, $R_7OSO_2$— and/or —$NR_5R_6$;

or $R_3$ is $C_2$–$C_6$haloalkanoyl, halobenzoyl, or a group

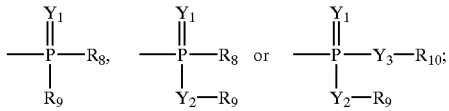

$Y_1$, $Y_2$ and $Y_3$ independently of each other are O or S;

$R'_3$ is phenylenedisulfonyl, naphthylenedisulfonyl,

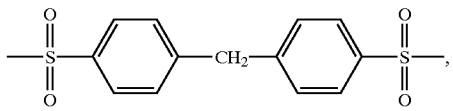

diphenylenedisulfonyl, or oxydiphenylenedisulfonyl, wherein these radicals are unsubstituted or substituted by $C_1$–$C_{12}$alkyl; or $R'_3$ is $C_2$–$C_{12}$alkylenedisulfonyl;

X is halogen;

$R_4$ is hydrogen, phenyl, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_{1-C12}$alkylsulfonyl, phenylsulfonyl, (4-methylphenyl)sulfonyl and/or by $C_2$–$C_6$alkanoyl;

or $R_4$ is $C_2$–$C_{18}$alkyl which is interrupted by one or more —O—, and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl and/or by $C_2$–$C_6$alkanoyl;

or $R_4$ is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_4$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_4$ is phenylsulfonyl, or (4-methylphenyl)sulfonyl;

$R_5$ and $R_6$ independently of each other are hydrogen or $C_1$–$C_{18}$alkyl which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_1$–$C_6$alkanoyl;

or $R_5$ and $R_6$ are $C_2$–$C_{18}$alkyl which is interrupted by one or more —O—, and which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_1$–$C_6$alkanoyl;

or $R_5$ and $R_6$ are $C_2$–$C_{18}$alkanoyl, which is unsubstituted or substituted by phenyl, OH, $C_1$–$C_{12}$-alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl;

or $R_5$ and $R_6$ are $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl;

or $R_5$ and $R_6$ are phenyl, benzoyl, phenylsulfonyl, (4-methylphenyl)sulfonyl, naphthylsulfonyl, anthracylsulfonyl or phenanthrylsulfonyl;

or $R_5$ and $R_6$, together with the nitrogen atom to which they are attached, form a 5-, 6- or 7-membered ring which may be interrupted by —O— or by —$NR_4$—;

$R_7$ is hydrogen, phenyl, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_7$ is $C_2$–$C_{18}$alkyl which is interrupted by one or more —O— and which unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_7$ is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_7$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl, and/or by $C_2$–$C_6$alkanoyl;

or $R_7$ is phenylsulfonyl, or (4-methylphenyl)sulfonyl;

$R_8$, $R_9$ and $R_{10}$ independently of one another are $C_1$–$C_6$alkyl which is unsubstituted or substituted by halogen;

or $R_8$, $R_9$ and $R_{10}$ are phenyl which is unsubstituted or substituted by $C_1$–$C_4$alkyl or halogen;

or $R_9$ and $R_{10}$ together are 1,2-phenylene or $C_2$–$C_6$alkylene which is unsubstituted or substituted by $C_1$–$C_4$alkyl or halogen.

The compounds of the formulae I, II and III are characterized in that they contain at least two halogen atoms on one of the carbon atoms next to the oximino group. Preferably the compounds contain three halogen atoms on one of the carbon atoms next to the oximino group.

$C_1$–$C_{18}$alkyl is linear or branched and is, for example, $C_1$–$C_8$-, $C_1$–$C_6$- or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl, preferably $C_1$–$C_4$alkyl, such as methyl, isopropyl or butyl.

$C_1$–$C_8$alkyl, $C_1$–$C_6$alkyl and $C_1$–$C_4$alkyl are likewise linear or branched and are, for example, as defined above up to the appropriate number of carbon atoms. Of interest are, for example, $C_1$–$C_8$-, especially $C_1$–$C_6$-, preferably $C_1$–$C_4$-alkyl, such as methyl or butyl. $R_1$ is for example $C_2$–$C_{12}$-, $C_4$–$C_{12}$-, $C_8$–$C_{12}$-, $C_4$–$C_8$-alkyl.

$C_2$–$C_{12}$alkyl, which is interrupted once or several times by —O—, is interrupted, for example, from one to five times, for example from one to three times or once or twice, by non-successive —O—. Accordingly, resulting structural units are for example: —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$CH$_2$CH$_3$, —[CH$_2$CH$_2$O]$_y$—CH$_3$, CH$_3$, wherein y=1–5, —(CH$_2$CH$_2$O)$_5$CH$_2$CH$_3$, —CH$_2$—CH(CH$_3$)—O—CH$_2$—CH$_2$—CH$_3$ or —CH$_2$—CH(CH$_3$)—O—CH$_2$—CH$_3$.

$C_3$–$C_{30}$cycloalkyl is a mono- or polycyclic aliphatic ring, for example a mono-, bi- or tricyclic aliphatic ring, e.g. $C_3$–$C_{20}$-, $C_3$–$C_{18}$-, $C_3$–$C_{12}$-, $C_3$–$C_{10}$cycloalkyl. Examples of monocyclic rings are cyclopropyl, cyclobutyl, cyclopentyl, cyclohexyl, or cycloheptyl, especially cyclopentyl and cyclohexyl. Examples of polycyclic rings are perhydroanthracyl, perhydrophenyathryl, perhydronaphthyl, perhydrofluorenyl, perhydrochrysenyl, perhydropicenyl, adamantyl, bicyclo[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl and the like. Also "spiro"-cycloalkyl compounds are covered by the definition $C_3$–$C_{30}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, page 11 and 12, wherein to the formulae (1)–(46) a bond to achieve the "yl" has to be added. The person skilled in the art is aware of this fact. In general, the cycloaliphatic rings may form repeating structural units.

$C_2$–$C_{12}$alkenyl radicals may be mono- or polyunsaturated, linear or branched and are for example $C_2$–$C_6$-, $C_2$–$C_6$- or $C_2$–$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_4$–$C_8$cycloalkenyl, may have one or more double bonds and is for example $C_4$–$C_6$-cycloalkenyl or $C_6$–$C_8$-cycloalkenyl. Examples are cyclobutenyl, cyclopentenyl, cyclohexenyl or cyclooctenyl, especially cyclopentenyl and cyclohexenyl, preferably cyclohexenyl.

$C_6$–$C_{12}$bicycloalkenyl refers to a bicyclic alkenyl group, which may possess one or more double bonds and wherein the double bonds are either situated in the same ring, but may also be situated in both rings. If several double bonds are present in the bicyclus, the double bonds are conjugated or non-conjugated, preferably the double bonds are conjugated. Examples are bicyclo[4.2.4]dodec-3,7-dien-5-yl, bicyclo[4.2.4]dodec-3-en-5-yl, bicyclo[4.2.4]dodec-4-en-6-yl, bicyclo[4.2.3]-non-3-en-5-yl, bicyclo[4.2.3]-non-4-en-6-yl, bicyclo[4.2.3]-non-7-en-8-yl, bicyclo[4.2.3]-non-8-en-7-yl, wherein the examples are referring to the following numbering

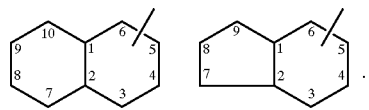

$C_2$–$C_{12}$alkylene is linear or branched and is, for example, $C_2$–$C_8$-, $C_2$–$C_6$- or $C_2$–$C_4$-alkylene. Examples are ethylene, propylene, butylene, pentylene, hexylene, heptylene, octylene, nonylene, decylene, undecylene and dodecylene. Preferred is $C_1$–$C_8$alkylene, especially $C_1$–$C_6$-alkylene, preferably $C_1$–$C_4$alkylene, such as methylene or butylene. $C_2$–$C_{12}$alkylenedisulfonyl accordingly is an alkylene radical as indicated above, which at both "yl"-moieties bears a sulfonyl group. Examples are —SO$_2$—(CH$_2$CH$_2$)$_z$—SO$_2$—, with z=1–6, e.g. —SO$_2$—CH$_2$CH$_2$—SO$_2$—, or —SO$_2$—CH(CH$_3$)CH$_2$—SO$_2$—.

Phenylenedisulfonyl, diphenylenedisulfonyl and oxy-diphenylendisulfonyl also bear the sulfonyl groups at the "yl" moiety. Accordingly, resulting structures are

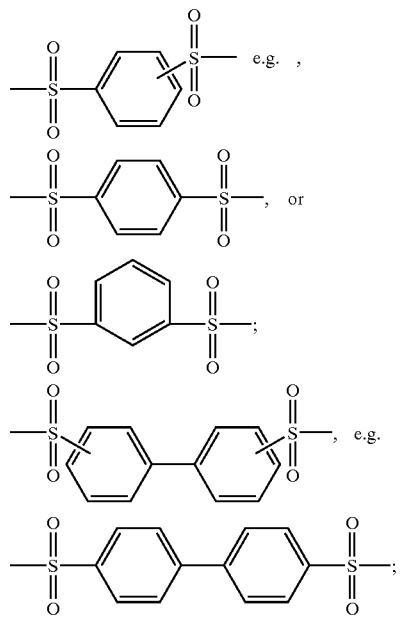

-continued

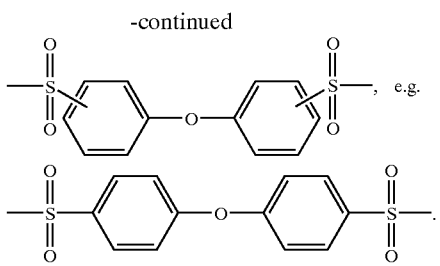, e.g.

Substituted phenyl carries from one to five, for example one, two or three, especially one or two, substituents on the phenyl ring. The substitution is preferably in the 4-, 3,4-, 3,5- or 3,4,5-position of the phenyl ring. The radicals $C_1$–$C_{18}$alkyl in the group $C_1$–$C_{18}$alkylsulfonyl are meant to be linear or branched and have the meanings described above. The radicals $C_3$–$C_{30}$cycloalkyl in the group $C_3$–$C_{30}$cyloalkylsulfonyl have the meanings described above.

When the radicals naphthyl, phenanthryl, heteroaryl and anthracyl are substituted by one or more radicals, they are, for example, mono- to penta-substituted, for example mono-, di- or tri-substituted, especially mono- or di-substituted.

When $R_1$ is a phenyl radical substituted by $OR_4$, $NR_5R_6$ and/or by $SR_7$ and the substituents $OR_4$, $NR_5R_6$ and $SR_7$ form 5- or 6-membered rings, via the radicals $R_4$, $R_5$, $R_6$ or $R_7$, with other substituents on the phenyl ring or with one of the carbon atoms of the phenyl ring, for example the following structural units are obtained

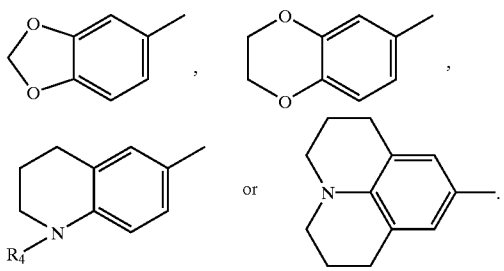

In the present application, the term "heteroaryl" denotes unsubstituted and substituted radicals, for example 3-thienyl, 2-thienyl,

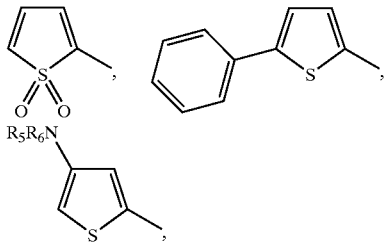

wherein $R_5$ and $R_6$ are as defined above, thianthrenyl, isobenzofuranyl, xanthenyl, phenoxanthiinyl,

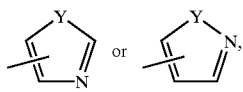

wherein Y is S, O or $NR_4$ and $R_4$ is as defined above. Examples thereof are pyrazolyl, thiazolyl, oxazolyl, isothiazolyl or isoxazolyl. Also included are, for example, furyl, pyrrolyl, 1,2,4-triazolyl,

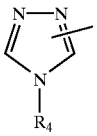

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

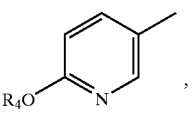

wherein $R_4$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

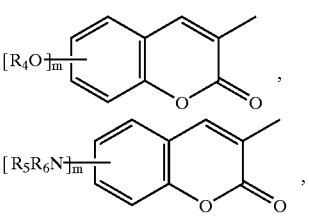

wherein m is 0 or 1 and $R_4$, $R_5$, $R_6$ are as defined above,

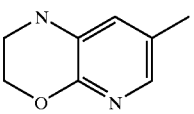

or anthraquinonyl. Each of the heteroaryls may carry the substituents indicated above or in claim 1.

Camphoryl, 10-camphoryl, are camphor-10-yl, namely

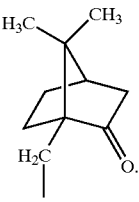

$C_2$–$C_6$alkanoyl is, for example, acetyl, propionyl, butanoyl or hexanoyl, especially acetyl.

$C_1$–$C_4$alkoxy is, for example, methoxy, ethoxy, propoxy and butoxy, it being possible for the alkyl radicals in alkoxy groups having more than two carbon atoms also to be branched.

$C_1$–$C_4$alkylhtio is for example, methylthio, ethylthio, propylthio and butylthio, it being possible for the alkyl radicals in alkylthio groups having more than two carbon atoms also to be branched.

$C_2$–$C_6$Alkoxycarbonyl is ($C_1$–$C_5$alkyl)-O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyl, it being possible for the alkyl radicals in alkoxy groups having more than two carbon atoms also to be branched.

$C_1$–$C_{10}$Haloalkyl and $C_1$–$C_4$haloalkyl are $C_1$–$C_{10}$- and $C_1$–$C_4$-alkyl mono- or poly-substituted by halogen, $C_1$–$C_{10}$- and $C_1$–$C_4$-alkyl being, for example, as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl. Preferred is $C_1$–$C_{10}$fluoroalkyl.

$C_2$–$C_6$haloalkanoyl is ($C_1$–$C_5$haloalkyl)-C(O)—, wherein $C_1$–$C_5$haloalkyl is as defined above up to the appropriate number of carbon atoms. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$–$C_4$haloalkyl, $C_1$–$C_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

Phenyl-$C_1$–$C_3$alkyl is, for example, benzyl, 2-phenylethyl, 3-phenylpropyl, α-methylbenzyl or α,α-dimethylbenzyl, especially benzyl.

Oxydiphenylene is

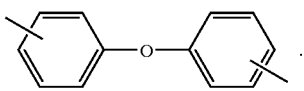

When $R_5$ and $R_6$ together with the nitrogen atom to which they are bonded form a 5-, 6- or 7-membered ring that may be interrupted by —O— or by —$NR_4$—, for example the following structures are obtained

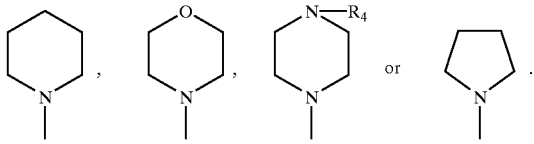

The definitions $C_1$–$C_{18}$alkylsulfonyl, phenyl-$C_1$–$C_3$alkylsulfonyl, camphorylsulfonyl, $C_1$–$C_{10}$haloalkylsulfonyl refer to the corresponding radicals $C_1$–$C_{18}$alkyl, phenyl-$C_1$–$C_3$alkyl, camphoryl and $C_1$–$C_{10}$haloalkyl, as described in detail above, being linked to a sulfonyl group (—$SO_2$—). Accordingly, also phenylsulfonyl, naphthylsulfonyl, anthracylsulfonyl and phenanthrylsulfonyl refer to the corresponding radicals linked to a sulfonyl group. $R_3$ is for example $C_2$–$C_{18}$-, $C_4$–$C_{12}$-, $C_6$–$C_{18}$-, $C_4$–$C_{10}$-alkylsulfonyl.

Groups having a —O—C-bond or a —O—Si-bond which cleaves upon the action of an acid, and being substituents of the radical $R_1$ are acid cleavable groups which increase the solubility of the compounds of formula I, II or III or Ib, IIb or IIIb (formulae Ib, IIb and IIIb are shown below) in the alkaline developer after reaction with an acid. This effect is for example described in U.S. Pat. No. 4,883,740. Examples of groups suitable as substitutents on the radical $R_1$ are for example known orthoesters, trityl and benzyl groups, tert.-butyl esters of carboxylic acids, tert.-butyl carbonates of phenols or silyl ethers of phenols, e.g. —$OSi(CH_3)_3$,

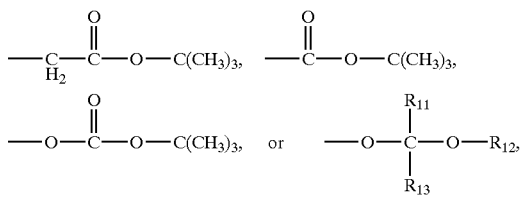

wherein $R_{11}$ and $R_{12}$ independently of one another are hydrogen, $C_1$–$C_6$alkyl, $C_3$–$C_8$cycloalkyl, phenyl-$C_1$–$C_3$alkyl, or $R_{11}$ and $R_{12}$ together are $C_2$–$C_5$alkylene, and $R_{13}$ is unsubstitued or halogen-substituted $C_1$–$C_{10}$alkyl, unsubstituted or halogen-substitued $C_3$–$C_8$cycloalkyl, or phenyl-$C_1$–$C_3$-alkyl, or, if $R_{11}$ and $R_{12}$ together are no $C_2$–$C_5$alkylene, $R_{13}$ and $R_{12}$ together may be $C_2$–$C_5$alkylene, which may be interrupted by an —O-atom or an —S-atom.

The terms "and/or" or "or/and" in the claims are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The invention also pertains to novel compounds of the formula Ib, IIb or IIIb

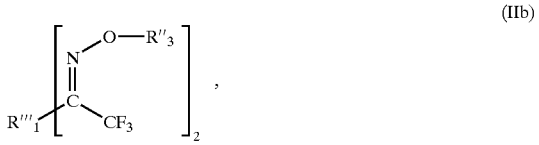

wherein

R"$_1$ is phenyl, which is unsubstituted or substituted by one or more $C_1$–$C_{12}$alkyl, phenyl-$C_1$–$C_3$-alkyl, $C_1$–$C_4$haloalkyl, halogen, phenyl, $OR_4$, $NR_5R_6$, $SR_7$, $SOR_7$, and/or $SO_2R_7$, optionally the substituents $OR_4$, $SR_7$ and $NR_5R_5$ form 5- or 6-membered rings via the radicals $R_4$, $R_5$, $R_6$ and/or $R_7$, with further substituents on the phenyl ring or with one of the carbon atoms of the phenyl ring;

or R"$_1$ is naphthyl, anthracyl or phenanthryl each of which is unsubstituted or substituted by $C_1$–$C_6$alkyl, phenyl, $OR_4$, $NR_5R_6$, $SR_7$, $SOR_7$ and/or $SO_2R_7$ optionally the substituted $OR_4$, $SR_7$ and $NR_5R_5$ form 5- or 6-membered rings via the radicals $R_4$, $R_5$, $R_6$ and/or $R_7$, with further substituents on the phenyl ring or with one of the carbon atoms of the naphthyl, anthracyl or phenanthryl ring or with one of the carbon atoms of the naphthyl, anthracyl or phenanthryl ring;

or R"$_1$ is a heteroaryl radical which is unsubstituted or substituted by $C_1$–$C_6$alkyl, phenyl, $OR_4$, $NR_5R_6$, $SR_7$, SOR$_7$, and/or SO$_2$R$_7$, optionally the substituents OR$_4$, SR$_7$ and NR$_5$R$_6$ form 5- or 6-membered rings, via the radicals R$_4$, R$_5$, R$_6$ and/or R$_7$ with further substituents on the heteroaryl ring or with one of the carbon atoms of the heteroaryl ring;

R'''$_1$ is phenylene, naphthylene,

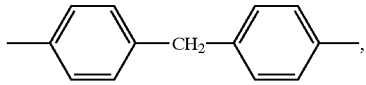

diphenylene or oxydiphenylene, wherein these radicals are unsubstituted or substituted by C$_1$–C$_{12}$alkyl;

or R'''$_1$ is

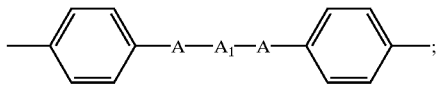

A is —O—, —S—, —NR$_4$—, —O(CO)—, —S(CO)—, —NR$_4$(CO)—, —SO—, —SO$_2$—, or —OSO$_2$—;

A$_1$ is C$_1$–C$_{12}$alkylene or C$_2$–C$_{12}$alkylene, which is interrupted by one or more —O—;

R''$_3$ is C$_1$–C$_{16}$alkylsulfonyl, phenyl-C$_1$–C$_3$alkylsulfonyl, camphorylsulfonyl, naphthylsulfonyl, trimethylphenylsulfonyl; or phenylsulfonyl which is substituted by one or more C$_2$–C$_{16}$alkyl, C$_1$–C$_4$alkoxy, C$_1$–C$_4$haloalkyl and/or halogen; and R'$_3$ is phenylenedisulfonyl, naphthylenedisulfonyl,

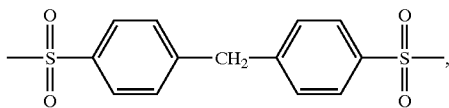

diphenylenedisulfonyl, or oxydiphenylenedisulfonyl, wherein these radicals are unsubstituted or substituted by C$_1$–C$_{12}$alkyl; or R'$_3$ is C$_2$–C$_{12}$alkylenedisulfonyl;

R$_4$ is hydrogen, phenyl,

C$_1$–C$_{12}$alkyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_1$–C$_{12}$alkylsulfonyl, phenylsulfonyl, (4-methylphenyl)sulfonyl and/or by C$_2$–C$_6$alkanoyl;

or R$_4$ is C$_2$–C$_{12}$alkyl which is interrupted by one or more —O—, and which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$ C$_1$–C$_{12}$alkylsulfonyl, phenylsulfonyl, (4-methylphenyl)sulfonyl and/or by C$_2$–C$_6$alkanoyl;

or R$_4$ is C$_2$–C$_{12}$alkanoyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_1$–C$_{12}$alkylsulfonyl, phenylsulfonyl, (4-methylphenyl)sulfonyl and/or by C$_2$–C$_6$alkanoyl;

or R$_4$ is C$_1$–C$_{12}$ alkylsulfonyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_{1-C12}$alkylsulfonyl, phenylsulfonyl, (4-methylphenyl)sulfonyl and/or by C$_2$–C$_6$alkanoyl;

or R$_4$ is phenylsulfonyl, or (4-methylphenyl)sulfonyl;

R$_5$ and R$_6$ independently of each other are hydrogen or C$_1$–C$_{12}$alkyl which is unsubstituted or substituted by OH, C$_1$–C$_4$alkoxy, C$_2$–C$_{12}$alkoxycarbonyl, phenoxy, phenoxycarbonyl, phenylthio, phenylthiocarbonyl, phenylamino, phenylaminocarbonyl, C$_1$–C$_{12}$alkylsulfonyl, phenylsulfonyl, (4-methylphenyl)sulfonyl and/or C$_1$–C$_6$alkanoyl;

or R$_5$ and R$_6$ are C$_2$–C$_{12}$alkyl which is interrupted by one or more —O—, and which is unsubstituted or substituted by OH, C$_1$–C$_4$alkoxy, C$_2$–C$_{12}$alkoxycarbonyl, phenoxy, phenoxycarbonyl, phenylthio, phenylthiocarbonyl, phenylamino, phenylaminocarbonyl, C$_1$–C$_{12}$alkylsulfonyl, phenylsulfonyl, (4-methylphenyl)sulfonyl and/or C$_1$–C$_6$alkanoyl;

or R$_5$ and R$_6$ are C$_2$–C$_{12}$alkanoyl which is unsubstituted or substituted by phenyl, OH, C$_1$–C$_{12}$-alkoxy, C$_2$–C$_{12}$alkoxycarbonyl, phenoxy, phenoxycarbonyl, phenylthio, phenylthiocarbonyl, phenylamino, phenylaminocarbonyl, C$_1$–C$_{12}$alkylsulfonyl, phenylsulfonyl, (4-methylphenyl)sulfonyl and/or by C$_2$–C$_6$alkanoyl;

or R$_5$ and R$_6$ are C$_1$–C$_{12}$ alkylsulfonyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, phenylamino, phenylaminocarbonyl, C$_1$–C$_{12}$alkylsulfonyl, phenylsulfonyl, (4-methylphenyl)sulfonyl and/or by C$_2$–C$_6$alkanoyl, or R$_5$ and R$_6$ are phenylsulfonyl, (4-methylphenyl)sulfonyl;

or R$_5$ and R$_6$ are phenyl, benzoyl, naphthylsulfonyl, anthracylsulfonyl or phenanthrylsulfonyl;

or R$_5$ and R$_6$, together with the nitrogen atom to which they are attached, form a 5-, 6- or 7-membered ring which optionally is interrupted by —O— or by —NR$_4$—;

R$_7$ is hydrogen, phenyl, C$_1$–C$_{12}$alkyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_1$–C$_{12}$alkylsulfonyl, phenylsulfonyl, (4-methylphenyl)sulfonyl and/or by C$_2$–C$_6$alkanoyl, or R$_7$ is C$_2$–C$_{12}$alkyl which is interrupted by one or more —O—, and which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_1$–C$_{12}$alkylsulfonyl, phenylsulfonyl, (4-methylphenyl)sulfonyl and/or by C$_2$–C$_6$alkanoyl;

or R$_7$ is C$_2$–C$_{12}$alkanoyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_1$–C$_{12}$alkylsulfonyl, phenylsulfonyl, (4-methylphenyl)sulfonyl and/or by C$_2$–C$_6$alkanoyl;

or R$_7$ is C$_1$–C$_{12}$ alkylsulfonyl which is unsubstituted or substituted by phenyl, OH, C$_1$–C$_{12}$alkoxy, C$_2$–C$_{12}$alkoxycarbonyl, phenoxy, phenoxycarbonyl, phenylthio, phenylthiocarbonyl, NR$_5$R$_6$, C$_{1-C12}$alkylsulfonyl, phenylsulfonyl, (4-methylphenyl)sulfonyl and/or by C$_2$–C$_6$alkanoyl;

or R$_7$ is phenylsulfonyl, or (4-methylphenyl)sulfonyl;

provided that if R''$_1$ is 4-methylphenyl or 4-octylphenyl, then R''$_3$ is not methanesulfonyl.

Oxime derivatives (of formulae I, Ib, II, IIb, III and IIIb) can generally be prepared by methods described in the literature, for example by reacting suitable free oximes ($R_3$ and $R'_3$=H) of formula X or XI with the desired (for example, sulfonic) acid halides of formula XV, XVI or XVII (for example, $R_3Cl$ or $Cl-R'_3-Cl$).

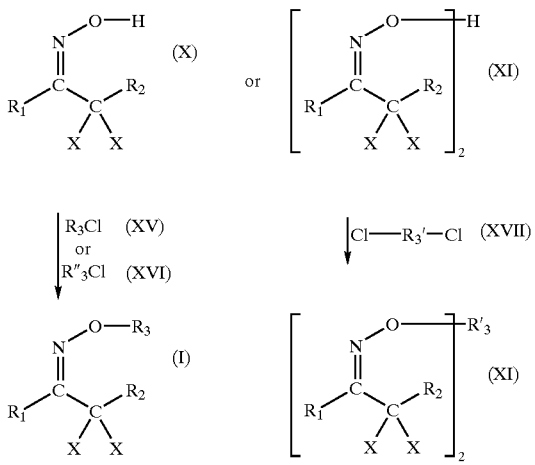

$R_1$, $R_2$, $R_3$, $R_3'$ and X are defined as described above. These reactions usually are carried out in an inert solvent such as for example toluene, tetrahydrofuran (THF) or dimethylformamide (DMF) in the presence of a base, for example a tertiary amine, such as triethylamine, or by reaction of the salt of an oxime with the desired acid chloride. These methods are disclosed, for example, in EP 48615. The sodium salts of oximes can be obtained, for example, by reacting the oxime in question with a sodium alcoholate in dimethylformamide. Such reactions are well known to those skilled in the art, and are generally carried out at temperatures in the range of −15 to +50° C., preferably 0 to 20° C.

The oximes required as starting materials can be obtained by a variety of methods described in standard chemistry textbooks (for instance in J. March, Advanced Organic Chemistry, 4th Edition, Wiley Interscience, 1992), or in specialized monographs, for example, S. R. Sandler & W. Karo, Organic functional group preparations, Vol. 3, Academic Press. One of the most convenient methods is, for example, the reaction of ketones with hydroxylamine or its salt in polar solvents like ethanol or aqueous ethanol. In that case, a base such as sodium acetate is added to control the pH of the reaction mixture. It is well known that the rate of the reaction is pH-dependent, and the base can be added at the beginning or continuously during the reaction. Basic solvents such as pyridine can also be used as base and/or solvent or cosolvent. The reaction temperature is generally the refluxing temperature of the mixture, usually about 60–120° C. Another convenient synthesis of oximes is the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis coll. vol V, pp 32 and 373, coll. vol. III, pp 191 and 513, coll. vol.II, pp. 202, 204 and 363, are suitable for the preparation of the oximes used as starting materials for the compounds according to the invention. Nitrous acid is usually generated from sodium nitrite. The alkyl nitrite can for example be methyl nitrite, ethyl nitrite, isopropyl nitrite, butyl nitrite, isoamyl nitrite.

The described syntheses can result in the formation of isomeric forms of the compounds of formula I, II and III or formula Ib, IIb and IIIb. The double bond of the oximino group can exist in both the syn (cis, Z) and the anti (trans, E) form or as mixtures of the two geometrical isomers. In the present invention, both the individual geometrical isomers and any mixtures of two geometrical isomers can be used. The invention accordingly also relates to mixtures of isomeric forms of the compounds of formula I, II and III or of compounds of formula Ib, IIb and IIIb.

The compounds of formula I, II and III or formula Ib, IIb, and IIIb of the individual geometrical isomers (Z and E forms) and any mixtures of two geometrical isomers can be used, however, it has been found that the compounds of formula I, II and III or formula Ib, IIb, and IIIb of a specific conformation (tentatively assigned as Z-form) are more thermally stable than the compounds of other conformation (tentatively assigned as E-form). Therefore, preferred use of the compounds of the present invention are of formula I, II and III or formula Ib, IIb, and IIIb of the single more thermally stable isomer (tentatively assigned as Z-form).

The syntheses of the oximes required as starting materials can result in the formation of a mixture of isomeric forms. Surprisingly, it has been found that the mixture of isomeric forms of the oximes required as starting materials is converted to a single isomeric form (tentatively assigned as Z-form) by treatment with acid. Using these oximes of the single isomer (Z-form) as the starting materials, the compounds of formula I, II and III or formula Ib, IIb, and IIIb of the thermally more stable single isomer are obtained. Accordingly the present invention also relates to a process for the synthesis of the thermally more stable isomer of the compounds of formula I, II and III or formula Ib, IIb, and IIIb by 1) conversion of the corresponding isomeric mixture of oximes to the oximes of the a single isomeric form by treatment with an acid, and 2) reaction of the oximes of the single isomeric form with the desired acid halides.

Subject of the invention therefore is a process for the specific preparation of the thermally stable isomer of the oxime ester compounds of formula I, II or III according to claim 1 or of the oxime ester compounds of formula Ib, IIb or IIIb according to claim 10, by (1) treating the isomeric mixture of the corresponding free oxime compounds of formula X or XI, obtained by conventional methods,

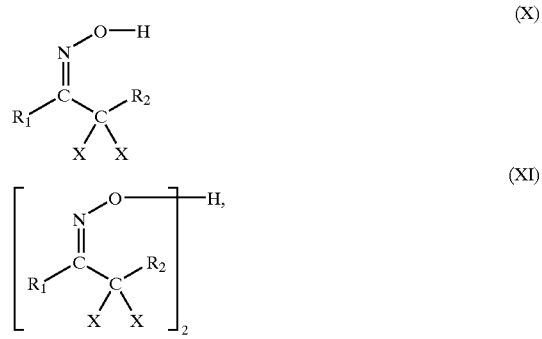

wherein $R_1$, $R_2$, and X are as defined above,
with an acid; and (2) reacting the thus prepared single isomeric free oxime compound with the corresponding acid halides of formula XV, XVI or XVII $$R_3Cl \quad (XV)$$

$$R''_3Cl \quad (XVI)$$

$$Cl-R'_3-Cl \quad (XVII),$$

wherein $R_3$ and $R'_3$ are as defined above and $R''_3$ is as defined below.

The conversion reactions of the isomeric mixture of oximes to the desired single isomer are usually carried out in an inert solvent such as methylene chloride, ethyl acetate, toluene, tetrahydrofuran or dimethylformamide in the presence of an acid such as hydrochloric acid, sulfuric acid, acetic acid, trifluoroacetic acid, or trifluoromethanesulfonic acid. Such reactions are usually carried out at temperature in the range of $-15°$ C. to $+120°$ C., preferably $0°$ C. to $80°$ C., more preferably $5°$ C. to $40°$ C. The compounds are isolated by methods known to the person skilled in the art, e.g. distillation, crystallisation, chromatographic methods. Examples for conventional methods to obtain the oxime compounds of formula X or XI as starting materials are given above.

Interesting are compounds of the formula Ib, IIb and IIIb, wherein $R_1$ is hydrogen, unsubstituted $C_2$–$C_{12}$alkyl; $C_1$–$C_{12}$alkyl which is substituted by $C_3$–$C_{30}$cycloalkyl; or $R_1$ is $C_2$–$C_{12}$alkenyl, $C_4$–$C_8$cycloalkenyl, $C_6$–$C_{12}$bicycloalkenyl, or camphoryl, or $R_1$ is phenyl which is substituted by one or more of the radicals $C_{10}$–$C_{12}$alkyl, $C_1$–$C_4$haloalkyl, chlorine, $OR_4$, $NR_5R_6$, $SR_7$ and/or —S-phenyl, optionally the substituents $OR_4$, $SR_7$ and $NR_5R_6$ form 5- or 6-membered rings, via the radicals $R_4$, $R_5$, $R_6$ and/or $R_7$, with further substituents on the phenyl ring or with one of the carbon atoms of the phenyl ring;

or $R_1$ is 2-naphthyl, anthracyl or phenanthryl, wherein the radicals 2-naphthyl, anthracyl and phenanthryl are unsubstituted or substituted by $C_1$–$C_6$alkyl, phenyl, $OR_4$, $NR_5R_6$, $SR_7$ and/or —S-phenyl, optionally the substituents $OR_4$, $SR_7$ and $NR_5R_6$ form 5- or 6-membered rings, via the radicals $R_4$, $R_5$, $R_6$ and /or $R_7$ with further substituents on the naphthyl, anthracyl or phenanthryl ring or with one of the carbon atoms of the naphthyl, anthracyl or phenanthryl ring;

or $R_1$ is a heteroaryl radical which is unsubstituted or substituted by $C_1$–$C_6$alkyl, phenyl, $OR_4$, $NR_5R_6$, $SR_7$ and/or —S-phenyl, optionally the substituents $OR_4$, $SR_7$ and $NR_5R_6$ form 5- or 6-membered rings, via the radicals $R_4$, $R_5$, $R_6$ and/or $R_7$ with further substituents on the heteroaryl ring or with one of the carbon atoms of the heteroaryl ring;

wherein all radicals $R_1$ with the exception of hydrogen can additionally be substituted by a group having a —O—C-bond or a —O—Si-bond which cleaves upon the action of an acid;

$R_4$ is phenyl, $C_2$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

or $R_4$ is $C_2$–$C_{12}$alkyl which is interrupted by one or more —O—, and which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_7$ is $C_2$–$C_{12}$alkyl which is unsubstituted or substituted by OH and/or $C_1$–$C_4$alkoxy;

or $R_7$ is $C_2$–$C_{12}$alkyl which is interrupted by one or more —O— and which is unsubstituted or substituted by OH and/or $C_1$–$C_4$alkoxy; and all other radicals are as described above.

Interesting are further compounds of formula Ib, IIb and IIIb, wherein $R_3$ is $C_2$–$C_{18}$alkylsulfonyl, $C_1$–$C_{10}$haloalkylsulfonyl, camphorylsulfonyl, phenyl-$C_{1-C3}$alkylsulfonyl, $C_3$–$C_{12}$cycloalkylsulfonyl, naphthylsulfonyl, anthracylsulfonyl or phenanthrylsulfonyl, wherein the groups cycloalkyl, naphthyl, anthracyl and phenanthryl of the radicals $C_3$–$C_{12}$cycloalkylsulfonyl, phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_4$, $COOR_7$, $C_1$–$C_4$alkyl-(OC)O—, $R_7OSO_2$— and/or —$NR_5R_6$;

or $R_3$ is phenyl substituted by one or more halogen, $C_1$–$C_4$haloalkyl, CN, $NO_2$, $C_2$–$C_{16}$alkyl, phenyl, $C_1$–$C_4$alkylthio, $OR_4$, $COOR_7$, $R_7OSO_2$— and/or —$NR_5R_6$;

or $R_3$ is $C_2$–$C_6$haloalkanoyl, or halobenzoyl;

$R_4$ is phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl; or $R_4$ is $C_2$–$C_{12}$alkyl which is interrupted by one or more —O—, and which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl; and all other radicals are as defined above.

Of special interest are compounds of the formula I, Ib, II, IIb, III or IIIb, wherein $R_1$ is phenyl which is unsubstituted or substituted by one or more of the radicals $C_{1-C12}$-alkyl, phenyl-$C_1$–$C_3$-alkyl, halogen, $OR_4$, $NR_5R_6$, $SR_7$, $SOR_7$, and/or $SO_2R_7$, optionally the substituents $OR_4$, form a 6-membered ring, via the radicals $R_4$; or $R_1$ is naphthyl or thienyl;

$R'_1$ is

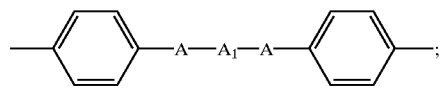

A is —O—, or —S—;

$A_1$ is $C_1$–$C_{12}$alkylene;

$R_2$ is halogen or $C_1$–$C_{10}$haloalkyl;

$R_3$ is $C_1$–$C_{18}$alkylsulfonyl, camphorylsulfonyl, phenyl-$C_1$–$C_3$alkylsulfonyl, phenylsulfonyl, naphthylsulfonyl, wherein the group phenyl of the radical phenylsulfonyl is unsubstituted or substituted by $C_1$–$C_{16}$alkyl, or $OR_4$;

$R'_3$ is phenylenedisulfonyl;

X is fluoro;

$R_4$ is phenyl, $C_1$–$C_{18}$alkyl which is unsubstituted or substituted by $C_2$–$C_{12}$alkoxycarbonyl; or $R_4$ is $C_2$–$C_{18}$alkyl which is interrupted by one or more —O—, and which is substituted by phenyl;

$R_5$ and $R_6$ are $C_1$–$C_{18}$alkyl;

$R_7$ is phenyl, or $C_1$–$C_{18}$alkyl.

Preferred are compounds of the formula I, Ib, II, IIb, III or IIIb, wherein

R₁ is phenyl, which is unsubstituted or substituted by one or more of the radicals $C_1$–$C_{12}$alkyl, halogen, $OR_4$, or $SR_7$;

$R_2$ is fluoro or $C_1$–$C_6$fluoroalkyl;

$R_3$ is $C_1$–$C_{12}$alkylsulfonyl, camphor-10-ylsulfonyl, naphthylsulfonyl, phenylsulfonyl wherein the group phenyl of this radical is unsubstituted or substituted by one or more $C_1$–$C_{16}$alkyl or $OR_4$;

X is fluorine;

$R_4$ is $C_1$–$C_4$alkyl;

$R_7$ is $C_1$–$C_4$alkyl;

i) if $R_1$ is phenyl, 4-methylphenyl, (methylthio)phenyl, and $R_2$ and X are both fluorine, then $R_3$ is not 4-methylphenylsulfonyl;

ii) if $R_1$ is 4-methylphenyl or 4-octylphenyl and $R_2$ and X are both fluorine, then $R_3$ is not 4-methylsulfonyl;

iii) if $R_1$ is phenyl, 4-methylphenyl, 4-methoxyphenyl, 4-chlorophenyl, trifluoromethyl or cyclohexyl and $R_2$ and X are both fluorine, then $R_3$ is not phenylsulfonyl;

vi) if $R_1$ is phenyl and $R_2$ is pentafluoroethyl and X is fluorine, then $R_3$ is not phenylsulfonyl;

Especially preferred are 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate; 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl) sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl) sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl) sulfonate; 2,2,2-trifluoro-=-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl) sulfonate; 2,2,2-trifluoro-1-(4-methoxyphenyl)-ethanone oxime-O-octylsulfonate; 2,2,2-trifluoro-1-(4-thiomethylphenyl)-ethanone oxime-O-(4-methoxyphenyl) sulfonate; 2,2,2-trifluoro-1-(4-thiomethylphenyl)-ethanone oxime-O-(4-dodecylphenyl)sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)-ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxyphenyl)-2,2,2-trifluoro ethanone oxime-O-sulfonyl]phenyl;

ethanone oxime-O-methylsulfonate; 2,2,3,3,4,4,4-heptafluoro-1-phenyl-butanone oxime-O-(10-camphorylsulfonate); 2,2,2-tri-fluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)

2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,-7H-5,8-dioxonaphth-2-yl]-ethanone oxime-O-propylsulfonate; 2,2,2-trifluoro-1-[4-methoxycarbonylmethoxyphenyl)-ethanone oxime-O-propylsulfonate; 2,2,2-trifluoro-1-[4-

(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxa-thiophen-2-yl)]-ethanone oxime-O-propylsulfonate. Evidently, the methylsulfonyl, methoxy, ethoxy or methylcarbonyl groups can also be replaced by other longer chain alkylsulfonyl, alkoxy or alkylcarbonyl groups. Also the methyl or propyl groups of the oxime-O-alkylsulfonate groups may easily be replaced by other alkyl groups.

The compounds of formulae I, II or III can be used as photosensitive acid donors in a photoresist. Resist systems can be prepared by image-wise irradiation of systems comprising compounds of formulae I, II or III, followed by a developing step.

A chemically amplified photoresist is understood to be a resist composition wherein the radiation sensitive component provides a catalytic amount of acid which subsequently catalyses a chemical reaction of at least one acid-sensitive component of the resist. Resulting is the induction of a solubility difference between the irradiated and non-irradiated areas of the resist. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during resist storage or during processing, which—in most cases—requires a post exposure bake step to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

In contrast, positive resist materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such resist and the reaction proceeds typically without a post exposure bake here, the requirements regarding chemical and thermal stability of the latent acid are less demanding than for chemically amplified positive resists. These resists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified resists.

From the above it becomes clear that chemical and thermal stability of a latent catalyst is vital for a chemically amplified resist and that latent acids which can work in a non-chemically amplified resist are not necessarily applicable to chemically amplified resists because of the different acid diffusion requirements, acid strength requirements and thermal and chemical stability requirements.

Preference is given to photoresist compositions, wherein the compounds of formula I, II and III $R_1$ is phenyl which is unsubstituted or substituted by $C_1$–$C_6$alkyl, phenyl, $OR_4$, $SR_7$, —S-phenyl, halogen and/or by $NR_5R_6$, optionally the substituents $OR_4$, and $NR_5R_6$ form 5- or 6-membered rings, via the radicals $R_4$, $R_5$ and/or $R_6$ with further substituents of the phenyl ring, or with one of the carbon atoms of the phenyl ring.

Other interesting photoresist compositions are those wherein in the compounds of formula I, II, and III $R_3$ is $C_1$–$C_{18}$ alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$-alkylthio, $OR_4$, $COOR_7$, $C_1$–$C_4$alkyl-OCO—, $R_7OSO_2$— and/or —$NR_5R_6$.

Preferred chemically amplified photoresist compositions of the present invention are those comprising compounds of the formula I, II and III wherein X and $R_2$ are both fluorine. To such compounds is referred as compounds of the formula Ia, IIa and IIIa

(Ia)

(IIa)

(IIIa)

wherein $R_1$, $R'_1$, $R_3$ and $R'_3$ are as defined above.

Particularly preferred are chemically amplified photoresist compositions comprising at least one compound of formula Ia wherein $R_1$ is unsubstituted phenyl or phenyl substituted once or more by $C_1$–$C_4$alkyl, $C_1$–$C_4$alkoxy, $C_1$–$C_4$alkylthio or halogen;

$R_3$ is $C_1$–$C_{16}$alkylsulfonyl, $C_3$–$C_{30}$cycloalkylsulfonyl, phenyl-$C_1$–$C_3$alkylsulfonyl, camphorylsulfonyl, naphthylsulfonyl or phenylsulfonyl; wherein these radicals are unsubstituted or substituted by $C_1$–$C_{12}$alkyl, $C_1$–$C_4$alkoxy, $C_1$–$C_4$haloalkyl, $C_1$–$C_4$alkylthio, $NO_2$ or halogen.

In other preferred compositions according to the invention the radicals $R_1$ with the exception of hydrogen are substituted by a group having a —O—C-bond or a —O—Si-bond which cleaves upon the action of an acid.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive. The invention accordingly relates to a chemically amplified positive photoresist.

If, on the other hand, the components of the formulation reduce the solubility of the composition after irradiation, the resist is negative. The invention accordingly relates also to a chemically amplified negative photoresist.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photoresist composition, comprising
- (a1) at least one polymer having acid-labile groups which decompose in the presence of an acid and increase the solubility of the resist film in an aqueous alkaline developer solution in the exposed area and
- (b) at least one compound of formula I, II or III.

A further embodiment of the invention is a chemically amplified positive alkaline-developable photoresist composition, comprising
- (a2) at least one monomeric or oligomeric dissolution inhibitor having at least one acid-labile group which decomposes in the presence of acid and increases the solubility in an aqueous alkaline developer solution and at least one alkali-soluble polymer and,
- (b) at least one compound of formula I, II or III.

Another specific embodiment of the invention resides in a chemically amplified positive alkaline-developable photoresist composition, comprising
- (a1) at least one polymer having acid labile groups which decompose in the presence of an acid and increase the solubility in an alkaline developer in the exposed area;
- (a2) a monomeric or oligomeric dissolution inhibitor, having at least one acid labile group, which decomposes in the presence of an acid and increase the alkaline solubility in the exposed area;
- (a3) an alkali-soluble monomeric, oligomeric or polymeric compound at a concentration which still keeps the resist film in the unexposed area essentially insoluble in the alkaline developer, and
- (b) at least one compound of formula I, II or III.

The invention therefore pertains to a chemically amplified photoresist composition, comprising
- (a1) at least one polymer having an acid-labile group which decomposes in the presence of an acid to increase the solubility in aqueous alkaline developer solution and/or
- (a2) at least one monomeric or oligomeric dissolution inhibitor having an acid-labile group which decomposes in the presence of an acid to increase the solubility in aqueous alkaline developer solution and/or
- (a3) at least one alkali-soluble monomeric, oligomeric or polymeric compound; and
- (b) as photosensitive acid donor, at least on e compound of formula I, II or III.

The compositions may comprise additionally to the component (b) other photosensitive acid donors and/or (c) other additives.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP 254853, EP 878738, EP 877293, JP-A-2-25850, JP-A-3-223860, and JP-A-4-251259.

The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically>110° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:
1) monomers that contain acid-labile groups which decompose in the presence of an acid to increase the solubility in aqueous alkaline developer solution and
2) monomers that are free of acid labile groups and free of groups that contribute to the alkaline solubility and/or 3) monomers that contribute to aqueous alkaline solubility of the polymer.

Examples of monomers of type 1) are: non-cyclic or cyclic secondary and tertiary-alkyl (meth)acrylates such as butyl acrylate, including t-butyl acrylate, butyl methacrylate, including t-butyl methacrylate, 3-oxocyclohexyl (meth) acrylate, tetrahydropyranyl (meth)acrylate, 2-methyl-adamantyl (meth)acrylate, cyclohexyl (meth)acrylate, norbornyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxy-carbonylstyrenes such as o-/m-/p-butoxycarbonylstyrene, including p-t-butoxycarbonylstyrene, o-/m-/p-(3-oxocyclohexyloxycarbonyl)styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, , o-/m-/p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such aso/m/p-butoxycarbonylmethoxystyrene, p-t-butoxycarbonylmethoxystyrene, o-/m-/p-(3-oxocyclohexyloxycarbonylmethoxy)styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)styrene, p- or m-(1-methoxy-1-methylethoxy)-methylstyrene, p- or m-(1-methoxy-1-methylpropoxy)styrene, p- or m-(1-methoxy-1-methylpropoxy)methylstyrene, p- or m-(1-methoxyethoxy) styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy) styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1-metylethoxy)-methylstyrene, p- or m-(1-n-propoxyethoxy) styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy) styrene, p- or m-(1-isopropoxy-1-methylporpoxy)-methylstyrene, p- or m-(1-isopropoxypropoxy)styrene, p- or m-(1-isopropoxyporpoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tertbutoxy-1-methylethoxy)styrene, p- or m-(1-n-pentoxy-1-methylethoxy)styrene, p- or m-(1-isoamyloxy-1-methylethoxy)styrene, p- or m-(1-n-hexyloxy-1-methylethoxy)styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP 829766. Examples of polymers with acetal blocking groups are given in U.S. Pat. No. 5,670,299, EP 780732, U.S. Pat. Nos. 5,627,006, 5,558,976, 5,558,971, 5,468,589, EP 704762, EP 762206, EP 342498, EP 553737 and described in ACS Symp. Ser. 614, Microelectronics Technology, pp. 35–55 (1995) and J. Photopolymer Sci. Technol. Vol. 10, No. 4 (1997), pp. 571–578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro-and Nanopatterning Polymers), p. 78–94, 1997; H.-T. Schacht, N. Muenzel, P. Falcigno, H. Holzwarth, and J. Schneider, J. Photopolymer Science and Technology, Vol.9, (1996), 573–586. This crosslinked system is preferred from the standpoint of heat resistance of the resist patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Examples of comonomers according to type 2) are: aromatic vinyl monomers, such as styrene, x-methylstyrene, acetoxystyrene, α-methylnaphthylene, acenaphthylene, vinyl alicyclic compounds such as vinyl norbornane, vinyl adamantane. vinyl cyclohexane, alkyl (meth)acrylates such as methyl methacrylate, acrylonitrile, vinylcyclohexane, vinylcyclohexanol, as well as maleic anhydride.

Examples of comonomers according to type 3) are: vinyl aromatic compounds such as hydroxystyrene, acrylic acid compounds such as methacrylic acid, ethylcarbonyloxystyrene and derivatives of thereof. These polymers are described, for example, in U.S. Pat. Nos. 5,827,634, 5,625, 020, 5,492,793, 5,372,912, EP 660187, U.S. Pat. No. 5,679, 495, EP 813113 and EP 831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol %. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development. Preferably the copolymers which have acid labile groups have a Mw of from about 3,000 to about 200,000, more preferably from about 5,000 to about 50,000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a Mw of from about 8,000 to about 50,000, and a molecular weight distribution of about 3 or less. Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyl-adamantyl group or an 1-ethoxy-ethoxy group and a tetrahydropyranyloxy group. A mixture of a non-crosslinked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility. Examples of polymer blends with polymers having different acid-labile groups are given in EP 780732, EP 679951 and U.S. Pat. No. 5,817,444.

Preferably monomeric and oligomeric dissolution inhibitors (a2) are used in the present invention. The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3,000 or lower, preferably from 100 to 3,000, more preferably from 200 to 2,500.

Examples of monomeric and oligomeric dissolution inhibitors having acid-labile groups are described as formulae (I) to (XVI) in EP 0831369. Other suitable dissolution inhibitors having acid-labile groups are shown in U.S. Pat. Nos. 5,356,752, 5,037,721, 5,0155,54, JP-A-1-289946, JP-A-1-289947, JP-A-2-2560, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-12357 and Japanese Patent Applications Nos. 3-33229, 3-230790, 3-320438, 4-254157, 4-52732, 4-103215, 4-104542, 4-107885, 4-107889, 4-152195, 4-254157, 4-103215, 4-104542, 4-107885, 4-107889, and 4-152195.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the oxime derivatives of formula I, II or III, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (a3) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen-or alkyl-substituted poly(hydroxystyrene)s, hydroxystyrene/N-substituted maleimide copolymers, o/p- and m/p-hydroxystyrene copolymers, partially o-alkylated poly(hydroxystyrene)s, [e.g., o-methylated, o-(1-methoxy)ethylated, o-(1-ethoxy)ethylated, o-2-tetrahydropyranylated, and o-(t-butoxycarbonyl)methylated poly(hydroxystyrene)s having a degree of substitution of from 5 to 30 mol % of the hydroxyl groups], o-acylated poly(hydroxystyrene)s [e.g., o-acetylated and o-(t-butoxy)carbonylated poly(hydroxystyrene)s having a degree of substitution of from 5 to 30mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. Further suitable are poly (meth)acrylic acid [e.g. poly(acrylic acid)], (meth)acrylic acid/(meth)acrylate copolymers [e.g. acrylic acid/methyl acrylate copolymers, methacrylic acid/methyl methacrylate copolymers or methacrylic acid/methyl methacrylate/t-butyl methacrylate copolymers], (meth)acrylic acid/alkene copolymers [e.g. acrylic acid/ethylene copolymers], (meth)acrylic acid/(meth)acrylamide copolymers [e.g. acrylic acid/acrylamide copolymers], (meth)acrylic acid/vinyl chloride copolymers [e.g. acrylic acid/vinyl chloride copolymers], (meth)acrylic acid/vinyl acetate copolymer [e.g. acrylic acid/ vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples. Especially preferred alkali-soluble polymers (a3) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly (hydroxystyrene)s, partially o- or m-alkylated and o- or m-acylated poly(hydroxystyrene)s, styrene/hydroxystyrene copolymer, and (α-methylstyrene/hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples. Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde. These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1,000 to 30,000. If the weight-average molecular weight thereof is lower than 1,000, the film reduction at unexposed parts during development is liable to be large. If the weight-average molecular weight there of exceeds 50,000, the developing rate may be too low. The especially preferred range of the molecular weight of the novolak resin is from 2,000 to 20,000. The poly(hydroxystyrene)s and derivatives and copolymers thereof shown above as alkalisoluble polymers other than novolak resins each have a weight-average molecular weight of 2,000 or higher, preferably from 4,000 to 200,000, more preferably from 5,000 to 50,000. From the standpoint of obtaining a polymer film having improved heat resistance, the weight-average molecular weight thereof is desirably at least 5,000 or higher. Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution. In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85%by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The content of the oxime derivatives of formula I, II, or III, (component (b)) in the positive resist according to the present invention is preferably between 0.01% to 20% by weight, based on the total amount of all solid components in the photoresist.

The use of the oxime derivatives according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP 361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

Acid-sensitive components that produce a negative resist characteristically are especially compounds which, when catalysed by an acid (e.g. the acid formed during irradiation of the compounds of formulae I, II or III), are capable of undergoing a crosslinking reaction with themselves and/or with one or more further components of the composition. Compounds of this type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of this type are generally known and are described, for example, in "Ullmann's Encyclopädie der technischen Chemie" [Ullmanns Enceclopedia of Technical Chemistry], 4th Edition, Vol. 15 (1978), p. 613–628. The crosslinker components should generally be present in a concentration of from 2 to 40, preferably from 5 to 30, percent by weight, based on the total solids content of the negative resist composition.

The invention thus includes, as a special embodiment, chemically amplified negative, alkali-developable photoresists, comprising (a4) an alkali-soluble resin as binder (a5) a component that when catalysed by an acid undergoes a crosslinking reaction with itself and/or with the binder, and (b) as photosensitive acid donor an oxime derivative of formula I, II or III.

The composition may comprise additionally to the component (b) other photosensitive acid donors and/or (c) other additives.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl)melamine and tetramethoxymethyl glucoril and N,N'-dimethoxymethylurone are the acid-curable resins given the greatest preference.

The concentration of the compound of formula I, II or IIII in negative resists in general is from 0.1 to 30, preferably up to 20, percent by weight, based on the total solids content of the compositions. From 1 to 15 percent by weight is especially preferred.

Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, for example homopolymers of vinyl- and 1-propenyl-substituted phenols, such as p-vinylphenol or p-(1-propenyl) phenol or copolymers of these phenols with one or more ethylenically unsaturated materials, for example styrenes. The amount of binder should generally be from 30 to 95 percent by weight or, preferably, from 40 to 80 percent by weight.

An especially preferred negative resist composition comprises from 0.5 to 15 percent by weight of an oxime derivative of formula I, II or III (component (b)), from 40 to 99 percent by weight of a phenolic resin as binder (component (a4)), for example one of those mentioned above, and from 0.5 to 30 percent by weight of a melamine resin (component (a5)) as cross-linking agent, the percentages relating to the solids content of the composition. With novolak or especially with polyvinyl phenol as binder, a negative resist having especially good properties is obtained.

Oxime derivatives can also be used as acid generators, which can be activated photochemically, for the acid-catalysed crosslinking of, for example, poly(glycidyl) methacrylates in negative resist systems. Such crosslinking reactions are described, for example, by Chae et al. in Pollimo 1993, 17(3), 292.

The positive and the negative resist compositions may comprise in addition to the photosensitive acid donor compound of formula I, II and III further photosensitive acid donor compounds (b1), further additives (c), other photoinitiators (d), and/or sensitizers (e). Therefore, subject of the invention also are chemically amplified resist compositions as described above, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

Oxime derivatives of the present invention in the positive and negative resist can also be used together with other, known photolatent acids (b1), for example, onium salts, 6-nitrobenzylsulfonates, bis-sulfonyl diazomethane compounds, cyano group-containing oximesulfonate compounds., etc. Examples of known photolatent acids for chemically amplified resists are described in U.S. Pat. Nos. 5,731,364, 5,800,964, EP 704762, U.S. Pat. Nos. 5,468,589, 5,558,971, 5,558,976 and particularly in EP 794457 and EP 795786. If a mixture of photolatent acids is used in the resist compositions according to the invention, the weight ratio of oxime derivatives of formula I, II or III to the other photolatent acid (b1) in the mixture is preferably from 1:99 to 99:1.

Examples of photolatent acids which are suitable to be used in admixture with the compounds of Formula I, II and III are (1) onium salt compounds, for example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxy-phenyl) benzylmethylsulfonium toluenesulfonate and the like. Particularly preferred are triphenylsulfonium triflate, diphenyliodonium hexafluoroantimonate.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methozyphenyl-bis(trichloromethyl)-s-triazine, naphthyl-bis(trichloromethyl)-s-triazine and the like; 1,1-bis(4-chlorophnyl)-2,2,2-trichloroethane; and the like.

(3) sulfone compounds, for example

β-ketosulfones, β-sulfonylsulfones and their α-diazo derivatives and the like. Preferred are phenacylphenylsulfone, mesitylphenacylsulfone, bis (phenylsulfonyl)methane, bis(phenylsulfonyl) diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsultonyloxy)7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N-(camphanylsulfonyloxy)succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2,2,1]-hept-5-ene-2,3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2,3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like. Other suitable sulfonate compounds preferably are, for example, benzoin tosylate, pyrogallol tristriflate, pyrogallolomethanesulfonic acid triester, nitorobenzyl-9,10-diethyoxyanthracene-2-sulfonate, α-(4-toluenesulfonyloxyimino)-benzyl cyanide, α-(4-toluenesulfonyloxyimino)-4-methoxybenzyl cyanide, α-(4-toluene-sulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsulfonyloxyimino-cyclohexa-2,5-dienylidene)-phenyl-acetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-methylsulfonyloxyimino-5H-thiophen-2-ylidene)-(2-chlorophenyl)-acetonitrile and the like. In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy) naphthylimide, N-(2-trifluoromethylphenylsulfonyloxy)phthalimide, N-(trifluoromethylsulfonyloxy)-bicyclo-[2,2,1]-hept-5-ene-2,3-dicarboximide, N-(camphanylsulfonyloxy) naphthylimide, N-(2-trifluoromethylphenylsulfonyloxy)phthalimide and the like.

(5) Quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone 2,2',3,4,-4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly) hydroxyphenylflavans such as 2,4,4-trimethyl-2',4',7-trihydroxy-2-phenylflavan, 2,4,4-trimethyl-2',4',5',6,7-pentahydroxy-2-phenylflavan and the like.

The positive and negative photoresist composition of the present invention may optionally contain one or more additives (c) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds. Further examples for organic basic compounds which can be used in the resist composition of the present invention are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoehtylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE 4408318, U.S. Pat. Nos. 5,609,989, 5,556,734, EP 762207, DE 4306069, EP 611998, EP 813113, EP 611998, and U.S. Pat. No. 5,498,506. However, the organic basic compounds suitable in the present invention are not limited to these examples. The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are liable to be caused. The composition can further contain a basic organic compound which decomposes under actinic radiation ("suicide base") such as for example described in EP 710885, U.S. Pat. Nos. 5,663,035, 5,595,855, 5,525,453, and EP 611998.

Examples of dyes (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (CI42555), methyl violet (CI 42535), rhodamine B (CI 45170B), malachite green (CI 42000), and methylene blue (CI52015).

Spectral sensitizers (e) may be further added to sensitize the photo latent acid to exhibit absorption in a region of longer wavelengths than far ultraviolet, whereby the photosensitive composition of the present invention can, for example, be rendered sensitive to an i-line or g-line radiation. Examples of suitable spectral sensitizers include benzophenones, p,p'-tetramethyldiaminobenzophenone, p,p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonylbis(5,7-dimethoxycarbonylcoumarin), 3-(aroylmethylene) thiazolines, eosin, rhodamine, erythrosine, and coronene. However, the suitable spectral sensitizers are not limited to these examples.

These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves.

Further suitable additives (c) are "acid-amplifiers", compounds that accelerate the acid formation or enhance the acid concentration. Such compounds may also be used in combination with the oxime derivatives of the formulae I, II, or III according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the oxime derivatives represented by formulae I, II or III according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc,. Japan), Fluorad FC 430 and FC431 (manufactured by Sumitomo 3M Ltd., Japan), Asahi Guard AG710 and Surflon S-382, SC101, SC102, SC103, SC104, SC105 , and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating). The amount applied (coating thickness) and the nature of the substrate (coating substrate) are dependent on the desired field of application. The range of coating thicknesses can in principle include values from approximately 0.01 µm to more than 100 µm.

After the coating operation generally the solvent is removed by heating, resulting in a layer of the photoresist on the substrate. The drying temperature must of course be lower than the temperature at which certain components of the resist might react or decompose. In general, drying temperatures are in the range from 60 to 160° C.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275–281 and by K. P. Nicolay in Offset Printing 1997, 6, pp. 34–37.

After the irradiation and, if necessary, thermal treatment, the irradiated sites (in the case of positive resists) or the non-irradiated sites (in the case of negative resists) of the composition are removed in a manner known per se using a developer. In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1–0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve$^{RTM}$/water.

Subject of the invention also is a process for the preparation of a photoresist by (1) applying to a substrate a composition as described above;

(2) post apply baking the composition at temperatures between 60° C. and 160° C.;

(3) image-wise irradiating with light of wavelengths between 150 nm and 1500 nm;

(4) optionally post exposure baking the composition at temperatures between 60° C. and 160° C.; and (5) developing with a solvent or with an aqueous alkaline developer.

Preferred is a process, wherein the image-wise irradiation is carried out with monochromatic or polychromatic radiation in the wavelength range from 190 to 450 nm, in particular in the range from 190 to 260 nm.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula Ib, IIb or IIIb as photolatent acid donors in compositions that can be crosslinked under the action of an acid and/or as dissolution enhancers in compositions wherein the solubility is increased under the action of an acid.

Subject of the invention further is a process of crosslinking compounds that can be crosslinked under the action of an acid, which method comprises adding a compound of formula Ib, IIb and/or IIIb to the above-mentioned compounds and irradiating imagewise or over the whole area with light having a wavelength of 150–1500 nm. The invention relates also to the use of compounds of formulae Ib, IIb or IIIb as photosensitive acid donors in the preparation of surface coatings, printing inks, printing plates, dental compositions, colour filters, resists or image-recording materials, or image-recording materials for recording holographic images, as well as to a process for the preparation of of surface coatings, printing inks, printing plates, dental compositions, colour filters, resists or image-recording materials, or image-recording materials for recording holographic images. Subject of the invention is also the use of compounds of formulae I, II or III as photosensitive acid donors in the preparation of colour filters or chemically amplified resist materials.

As already mentioned above, in photocrosslinkable compositions, oxime derivatives act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Oxime derivatives according to the present invention can also be used to produce so-called "print-out" images when the compound is used together with a colourant that changes colour when the pH changes, as described e.g. in JP Hei 4 328552-A or in U.S. Pat. No. 5,237,059. Such color-change systems can be used according to EP 199672 also to monitor goods that are sensitive to heat or radiation. In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with oxime derivatives can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, oxime derivatives that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acids of formula I, II or III, in particular the compounds of formula Ib, IIIb, according to the invention, are, for example, mixtures of polyfunctional alcohols or hydroxy-group-containing acrylic and polyester resins, or partially hydrolysed polyvinylacetals or polyvinyl alcohols with poly-functional acetal derivatives. Under certain conditions, for example the acid-catalysed self-condensation of acetal-functionalised resins is also possible.

Suitable acid-curable resins in general are all resins whose curing can be accelerated by acid catalysts, such as aminoplasts or phenolic resole resins. These resins are for example melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx, Lackkunstharze (Munich, 1971), pp. 86–123 and pp. 229–238, or in Ullmann, Encyclopädie der techn. Chemie, 4th Ed., Vol. 15 (1978), pp. 613–628, or Ullmann's Encyclopedia of Industrial Chemistry, Verlag Chemie, 1991, Vol. 18, p. 360 ff., Vol. A19, p. 371 ff.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I, II or III. In that process, radical polymerisation initiators or photoinitiators can additionally be used. The former initiate polymerisation of the unsaturated groups during heat treatment, the latter during UV irradiation.

The invention also relates to a composition comprising
  (a) a compound which cures upon the action of an acid or a compound whose solubility is increased upon the action of an acid; and
  (b) as photosensitive acid donor, at least one compound of the formula Ib, IIb or IIIb as described above.

The compounds of formulae I, II or III, or Ib, IIb or IIIb respectively, are generally added to the compositions in an amount from 0.1 to 30% by weight, for example from 0.5 to 10% by weight, especially from 1 to 5% by weight.

According to the invention, the compounds of formula I, Ib, II, IIb, III or IIIb can be used together with further photosensitive acid donor compounds (b1), further photoinitiators (d), sensitisers (e) and/or additives (c). Suitable photosensitive acid donor compounds (b1), sensitizers (e) and addtives (c) are described above.

Examples of additional photoinitiators (d) are radical photoinitiators, such as those from the class of the benzophenones, acetophenone derivatives, such as a-hydroxycycloalkylphenyl ketone, dialkoxyacetophenone, a-hydroxy- or a-amino-acetophenone, 4-aroyl-1,3-dioxolans, benzoin alkyl ethers and benzil ketals, monoacylphosphine oxides, bisacylphosphine oxides or titanocenes. Examples of especially suitable additional photoinitiators are: 1-(4-dodecylbenzoyl)-1-hydroxy-1-methyl-ethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methylethane, 1-[4-(acryloyloxyethoxy)-benzoyl]-1-hydroxy-1-methyl-ethane, diphenyl ketone, phenyl-1-hydroxy-cyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzoyl)-1-methyl-1-morpholino-ethane, benzil dimethyl ketal, bis(cyclopentadienyl)-bis(2,6-difluoro-3-pyrryl-phenyl) titanium, trimethylbenzoyldiphenylphosphine oxide, bis(2, 6-dimethoxy-benzoyl)-(2,4,4-trimethyl-pentyl)-phosphine oxide, bis(2,4,6-trimethylbenzoyl)-2,4-dipentyloxyphenyl-phosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators are peroxide compounds, e.g. benzoyl peroxide (other suitable peroxides are described in U.S. Pat. No. 4,950,581, col. 19, I. 17–25) or cationic photoinitiators, such as aromatic sulfonium or iodonium salts, such as those to be found in U.S. Pat. No. 4,950,581, col. 18, I. 60 to col. 19, I. 10, or cyclopentadienyl-arene-iron(II) complex salts, for example ($\eta^6$-isopropylbenzene) ($\eta^5$-cyclopentadienyl)-iron(II) hexafluorophosphate.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are
1. 2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1, 3,3-tetramethylbutyl)phenyl)-benzotriazole, 2-(3',5'-di-t-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(a,a-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxy-carbonylethyl)phenyl)-benzotriazole, 2-(3'-tert-butyl-5'-[2-(2-ethylhexyloxy) carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.
2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.
3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.
4. Acrylates, such as a-cyano-b,b-diphenylacrylic acid ethyl ester or isooctyl ester, a-carbomethoxy-cinnamic acid methyl ester, a-cyano-b-methyl-p-methoxy-cinnamic acid methyl ester or butyl ester, a-carbomethoxy-p-methoxy-cinnamic acid methyl ester, N-(b-carbomethoxy-b-cyanovinyl)-2-methyl-indoline.
5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl) sebacate, n-butyl-3,5-di-tert-butyl-4-hydroxybenzyl-malonic acid bis(1,2,2,6,6-pentamethylpiperidyl)ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2, 2,6,6-tetramethylpiperidyl)sebacate, bis(1-octyloxy-2,2, 6,6-tetramethylpiperidyl)succinate, condensation product of N,N'-bis(2,2,6,6-tetra-methyl-4-piperidyl) hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)-pyrrolidine-2,5-dione.

6. Oxalic acid diamides, such as 4,4'-dioctyloxy-oxanilide, 2,2'-diethoxy-oxanilide, 2,2'-di-oc-tyloxy-5,5'-di-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-di-substituted oxanilides.

7. 2-(2-Hydroxyphenyl)-1 3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl-phenyl)-1,3,5-triazine, 2-[2-hydroxy-4-(2-hydroxy-3-octyloxy-propyloxy)phenyl]-4,6-bis(2,4-dimeylphenyl)-1,3,5-triazine, 2-[4-dodecyl-/tridecyl-oxy-(2-hydroxypropyl)oxy-2-hydroxy-phenyl]-4,6-bis(2,4-dimethylphenyl)-1,3,5-triazine.

8. Phosphites and phosphonites, such as triphenyl phosphite, diphenyl alkyl phosphites, phenyl dialkyl phosphites, tris(nonylphenyl) phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl) pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069,954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP747771, JP7036179-A, EP619520, JP6161109-A, JP6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers and adhesion promoters.

For curing thick and pigmented coatings, the addition of micro glass beads or powdered glass fibres, as described in U.S. Pat. No. 5,013,768, is suitable.

Oxime derivatives can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

The compounds of formulae I, II or III can also be used for curing mouldings made from composites. A composite consists of a self-supporting matrix material, for example a glass fibre fabric, impregnated with the photocuring formulation.

It is known from EP 592139 that oxime derivatives can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds of formula I, II or III are also suitable for this application.

The oxime derivatives of the present invention can also be used to shape polymers that undergo an acid induced transition into a state where they have the required properties using photolithography. For instance the oxime derivatives can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers in the manufacturing of integrated circuits.

It is known that conjugated polymers like, e.g. polyanilines can be converted from semiconductive to conductive state by means of proton doping. The oxime derivatives of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable radiation sources for the compositions comprising compounds of formula I, II or III are radiation sources that emit radiation of a wavelength of approximately from 150 to 1500, for example from 180 to 1000, or preferably from 190 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiation sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emit at different wavelengths throughout the whole spectrum either as small band emitting source or as broad band (white light) source. Also suitable are laser radiation sources, for example excimer lasers, such as Kr-F lasers for irradiation at 248 nm, Ar-F lasers at 193 nm, or $F_2$ laser at 157 nm. Lasers in the visible range and in the infrared range can also be used. Especially suitable is radiation of the mercury i, h and g lines at wavelengths of 365, 405 and 436 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oxime derivatives in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures. The surface coating to be cured can be exposed directly to sunlight or daylight-equivalent light sources. The curing can, however, also take place behind a transparent layer (e.g. a pane of glass or a sheet of plastics).

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

2,2,2-Trifluoro-1-phenyl-ethanone oxime-O-methylsulfonate 1.1: 2,2,2-Trifluoro-1-phenyl-ethanone oxime 25 g (0.144 mol) of 2,2,2-Trifluoro-1-phenyl-ethanone are dissolved in 40 ml of ethanol at 80° C. To the solution are added dropwise 10.5 g (0.151 mol) of hydroxylammonium chloride and 20.1 g (0.245 mol) of sodium acetate dissolved in 20 ml of water. The reaction mixture is refluxed overnight, and the solvent is distilled off by a rotary evaporator. The residue is poured into water, the white precipitate is rinsed with water and dried under vacuum, yielding 24.4 g of 2,2,2-trifluoro-1-phenyl-ethanone oxime. The crude product is used in the next step without further purification.

1.2: 2,2,2-Trifluoro-1-phenyl-ethanone oxime-O-methylsulfonate 2.0 g (10.6 mmol) of 2,2,2-Trifluoro-1-phenyl-ethanone oxime are dissolved in 40 ml of tetrahydrofurane (THF) and cooled in an ice bath. To the solution are added 1.3 g (1 1.7 mmol) of methylsulfonyl chloride, followed by dropwise addition of 1.6 g (15.9 mmol) of triethylamine. The reaction mixture is stirred at 0° C. for 5 hours, poured into ice water, and extracted with ethyl acetate. The organic phase is washed with water and brine, dried over $MgSO_4$, and concentrated. The residue is purified by reprecipitation using methanol and water, yielding 2.3 g (8.6 mmol; 81%) of 2,2,2-trifluoro-1-phenyl-ethanone oxime-O-(methanesulfonate) as a white solid with a melting point (mp.) of 51–64° C. The structure is confirmed by the $^1$H-NMR spectrum ($CDCL_3$). δ [ppm]: 3.26 (s, 3H), 7.47–7.63 (m, 5H).

EXAMPLE 2

2,2,2-Trifluoro-1-phenyl-ethanone oxime-O-(10-camphorylsulfonate)

2.0 g (10.6 mmol) of 2,2,2-trifluoro-1-phenyl-ethanone oxime (prepared as described in example 1.1) are dissolved in 40 ml of THF and cooled in an ice bath. To the solution are added 2.9 g (11.6 mmol) of 10-camphorylsulfonyl chloride, followed by dropwise addition of 1.6 g (15.9 mmol) of triethylamine. The reaction mixture is stirred at 0° C. for 2.5 hours, poured into ice water, and extracted with ethyl acetate. The organic phase is washed with water and brine, dried over $MgSO_4$, and concentrated. The residue is purified by flash chromatography on silica gel with ethyl acetate and hexane (1:9) as eluent, yielding 2.2 g (5.5 mmol; 52%) of 2,2,2-trifluoro-1-phenyl-ethanone oxime-O-(10-camphorylsulfonate) as a pale yellow liquid. The structure is confirmed by the $^1$H-NMR spectrum ($CDCl_3$). δ [ppm]: 0.92 (s, 3H), 1.14(Z)/1.18(E) (s, 3H), 1.40–1.50 (m, 1H), 1.66–1.75 (m, 1H), 1.92–2.19 (m, 3H), 2.34–2.55 (m, 2H), 3.28(E)/3.33(Z) (d, 1H), 3.87(Z)/3.97(E) (d, 1H), 7.48–7.65 (m, 5H). The $^1$H-NMR reveals that the product is a 9:1 mixture of Z and E isomers. The signals are tentatively assigned to the E- and Z-conformations.

EXAMPLE 3

2,2,2-Trifluoro-1-phenyl-ethanone oxime-O-(4-methoxyphenylsulfonate)

2.0 g (10.6 mmol) of 2,2,2-trifluoro-1-phenyl-ethanone oxime (prepared as described in example 1.1) are dissolved in 40 ml of THF and cooled in an ice bath. To the solution are added 2.4 g (11.7 mmol) of 4-methoxyphenylsulfonyl chloride, followed by dropwise addition of 1.6 g (15.9 mmol) of triethylamine. The reaction mixture is stirred at 0° C. for 5 hours, poured into ice water, and extracted with ethyl acetate. The organic phase is washed with water and brine, dried over $MgSO_4$, and concentrated. The residue is purified by recrystallization from methanol, yielding 2.3 g (6.5 mmol; 61%) of 2,2,2-trifluoro-1-phenyl-ethanone oxime-O-(4-methoxyphenylsulfonate) as a white solid, mp. 69–73° C. The structure is confirmed by the $^1$H-NMR spectrum ($CDCl_3$). δ [ppm]: 3.92 (s, 3H), 7.05 (d, 2H), 7.38–7.58 (m, 5H), 7.95 (d, 2H).

EXAMPLE 4

2,2,2-Trifluoro-1-phenyl-ethanone oxime-O-(1-naphthylsulfonate)

2.0 g (10.6 mmol) of 2,2,2-trifluoro-1-phenyl-ethanone oxime (prepared as described in example 1.1) are dissolved in 40 ml of THF and cooled in an ice bath. To the solution are added 2.6 g (11.6 mmol) of 1-naphthylsulfonyl chloride, followed by dropwise addition of 1.6 g (15.9 mmol) of triethylamine. The reaction mixture is stirred at 0° C. for 4 hours, poured into ice water, and extracted with ethyl acetate. The organic phase is washed with water and brine, dried over $MgSO_4$, and concentrated. The residue is purified by reprecipitation using acetone and water, yielding 3.7 g (9.8 mmol; 92%) of 2,2,2-trifluoro-1-phenyl-ethanone oxime-O-(1-naphthylsulfonate) as white solid, mp. 96–104° C. The structure is confirmed by the $^1$H-NMR spectrum ($CDCl_3$). δ [ppm]: 7.23–7.38 (m, 2H), 7.43–7.85 (m, 6H), 7.95–8.05 (m, 1H), 8.18–8.27 (m, 1H), 8.37–8.83 (m, 2H).

EXAMPLE 5

2,2,2-Trifluoro-1-phenyl-ethanone oxime-O-(2-naphthylsulfonate)

2.0 g (10.6 mmol) of 2,2,2-trifluoro-1-phenyl-ethanone oxime (prepared as described in example 1.1) are dissolved in 40 ml of THF and cooled by ice bath. To the solution are added 2.6 g (11.6 mmol) of 2-naphthylsulfonyl chloride, followed by dropwise addition of 1.6 g (15.9 mmol) of triethylamine. The reaction mixture is stirred at 0° C. for 4 hours, poured into ice water, and extracted with ethyl acetate. The organic phase is washed with water and brine, dried over $MgSO_4$, and concentrated. The residue is purified by recrystallization from methanol, yielding 2.8 g (7.4 mmol; 70%) of 2,2,2-trifluoro-1-phenyl-ethanone oxime-O-(2-naphthylsulfonate) as white solid, mp. 117–120° C. The structure is confirmed by the $^1$H-NMR spectrum ($CDCl_3$). δ [ppm]: 7.37–7.58 (m, 5H), 7.64–7.78 (m, 2H), 7.92–8.09 (m, 4H), 8.63 (s, 1H).

EXAMPLE 6

2,2,2-Trifluoro-1-phenyl-ethanone oxime-O-(2,4,6-trimethylphenylsulfonate)

2.0 g (10.6 mmol) of 2,2,2-trifluoro-1-phenyl-ethanone oxime (prepared as described in example 1.1) are dissolved in 40 ml of THF and cooled in an ice bath. To the solution are added 2.5 g (11.6 mmol) of 2,4,6-trimethylphenylsulfonyl chloride, followed by dropwise addition of 1.6 g (15.9 mmol) of triethylamine. The reaction mixture is stirred at 0° C. for 4.5 hours, poured into ice water, and extracted with ethyl acetate. The organic phase is washed with water and brine, dried over $MgSO_4$, and concentrated. The residue is purified by reprecipitation using methanol and water, yielding 3.2 g (8.6 mmol; 81%) of 2,2,2-trifluoro-1-phenyl-ethanone oxime-O-(2,4,6-trimethylphenylsulfonate) as a white solid, mp. 90–103° C. The structure is confirmed by the $^1$H-NMR spectrum ($CDCl_3$). δ [ppm]: 2.34(E)/2.36(Z) (s, 3H), 2.60(Z)/2.68(E) (s, 6H), 7.00 (m, 2H), 7.40 (s, 2H), 7.47–7.58 (m, 3H). The $^1$H-NMR reveals that the product is a 4:1 mixture of Z and E isomers. The signals are tentatively assigned to the E- and Z-conformations.

EXAMPLE 7

2,2,2-Trifluoro-1-(4-methylphenyl)-ethanone oxime-O-(10-camphorylsulfonate)

7.1: 2,2,2-Trifluoro-1-(4-methylphenyl)-ethanone 50.0 g (0.543 mol) of toluene and 66.3 g (0.543 mol) of 4-dimethylaminopyridine are mixed in 700 ml of $CH_2Cl_2$ and cooled in a nice bath. To the solution are added dropwise 114.0 g (0.543 mol) of trifluoroacetic anhydride, followed by 167 g (1.25 mol) of $AlCl_3$ by portions. The reaction mixture is stirred at room temperature overnight, poured into ice water, and extracted with $CH_2Cl_2$. The organic phase is washed with water, dried over $MgSO_4$, and concentrated. The residue is distilled at 90° C./1 5 mm Hg, yielding 49.5 g of the product as a colorless liquid.

7.2: 2,2,2-Trifluoro-1-(4-methylphenyl)-ethanone oxime 49.5 g (0.263 mol) of 2,2,2-trifluoro-1-(4-methylphenyl)-ethanone are dissolved in 250 ml of ethanol at 80° C. To the solution are added dropwise 19.2 g (0.276 mol) of hydroxylammonium chloride and 36.7 g (0.447 mol) of sodium acetate dissolved in 125 ml of water. The reaction mixture is refluxed for 3.5 hours. The mixture is poured into ice water, affording a white solid. The filtration yields 39.2 g of 2,2,2-trifluoro-1-(4-methylphenyl)-ethanone oxime as a white solid, mp. 54–68° C. The crude product is used in the next step without further purification.

7.3: 2,2,2-Trifluoro-1-(4-methylphenyl)-ethanone oxime-O-(10-camphorylsulfonate)

3.0 g (14.8 mmol) of 2,2,2-trifluoro-1-(4-methylphenyl)-ethanone oxime are dissolved in 30 ml of THF and cooled by an ice bath. To the solution are added 4.1 g (16.2 mmol) of 10-camphorylsulfonyl chloride, followed by dropwise addition of 2.3 g (22.2 mmol) of triethylamine. The reaction mixture is stirred at 0° C. for 90 min, poured into ice water, and extracted with ethyl acetate. The organic phase is washed with water and brine, dried over $MgSO_4$, and concentrated. The residue is purified by flash chromatography on silica gel with ethyl acetate and hexane (1:9) as an eluent, yielding 3.29 (7.7 mmol; 52%) of 2,2,2-trifluoro-1-(4-methylphenyl)-ethanone oxime-O-(10-camphorylsulfonate) as a colorless liquid. The structure is confirmed by the $^1$H-NMR spectrum (CDCl$_3$). δ [ppm]: 0.92 (s, 3H), 1.14(Z)/1.18(E) (s, 3H), 1.42–1.50 (m, 1H), 1.64–1.74 (m, 1H), 1.93–2.18 (m, 3H), 2.35–2.56 (m, 5H), 3.28(E)/3.33(Z) (d, 1H), 3.87(Z)/3.94(E) (d, 1H), 7.27–7.32 (m, 2H), 7.43(Z)17.53(E) (d, 2H). The $^1$H-NMR reveals that the product is a 4:1 mixture of Z and E isomers. The signals are tentatively assigned to the E- and Z-conformations.

EXAMPLE 8

2,2,2-Trifluoro-1-(4-methylphenyl)-ethanone oxime-O-(methylsulfonate)

3.0 g (14.8 mmol) of 2,2,2-trifluoro-1-(4-methylphenyl)-ethanone oxime (prepared as described in example 7.2) are dissolved in 30 ml of THF and cooled by an ice bath. To the solution are added 1.9 g (16.2 mmol) of methylsulfonyl chloride, followed by dropwise addition of 2.3 g (22.2 mmol) of triethylamine. The reaction mixture is stirred at 0° C. for 4 hours, poured into ice water, and extracted with ethyl acetate. The organic phase is washed with water and brine, dried over $MgSO_4$, and concentrated. The residue is purified by flash chromatography on silica gel with ethyl acetate and hexane (15:85) as an eluent, yielding 2.6 g (9.2 mmol; 62%) of 2,2,2-trifluoro-1-(4-methylphenyl)-ethanone oxime-O-(methylsulfonate) as a white solid, mp. 56–67 ° C. The structure is confirmed by the $^1$H-NMR spectrum (CDCl$_3$). δ [ppm]: 2.42 (s, 3H), 3.27 (s, 3H), 7.26–7.53 (m, 4H).

EXAMPLE 9

2,2,2-Trifluoro-1-(2-methylphenyl)-ethanone oxime-O-(10-camphorylsulfonate)

9.1: 2,2,2-Trifluoro-1-(2-methylphenyl)-ethanone

A Grignard reagent is prepared from 25.0 g (0.146 mol) of 2-bromotoluene and 4.3 g (0.175 mol) of magnesium in 100 ml of diethyl ether. The Grignard reagent is added dropwise to a solution of 22.8 g (0.161 mol) ethyl trifluoroacetate in 120 ml of diethyl ether at −78° C. The reaction mixture is allowed to warm to room temperature and stirred for one additional hour. 300 ml of $NH_4Cl$ aq and 100 ml of 1N HCl are then added to the mixture. The aqueous phase is removed, the organic phase is washed with $NH_4Cl$ aq and brine, dried over $MgSO_4$, and concentrated. The residue is purified by flash chromatography on silica gel with hexane as an eluent, yielding 6.3 g of 2,2,2-trifluoro-1-(2-methylphenyl)-ethanone as colorless liquid.

9.2: 2,2,2-Trifluoro-1-(2-methylphenyl)-ethanone oxime 3.7 g (0.020 mol) of 2,2,2-trifluoro-1-(2-methylphenyl)-ethanone are dissolved in 20 ml of ethanol at 80° C. To the solution are added dropwise 1.4 g (0.020 mol) of hydroxylammonium chloride and 2.7 g (0.033 mol) of sodium acetate dissolved in 10 ml of water. The reaction mixture is refluxed for 5 hours, poured into ice water, and extracted with ethyl acetate. The organic phase is washed with water and brine, dried over $MgSO_4$, and concentrated, yielding 2.7 g of 2,2,2-trifluoro-1-(2-methylphenyl)-ethanone oxime as a white solid. The crude product is used in the next reaction step without further purification.

9.3: 2,2,2-Trifluoro-1-(2-methylphenyl)-ethanone oxime-O-(10-camphorylsulfonate)

1.2 g (5.9 mmol) of 2,2,2-trifluoro-1-(2-methylphenyl)-ethanone oxime are dissolved in 30 ml of THF and cooled by ice bath. To the solution are added 1.6 g (6.5 mmol) of 10-camphorylsulfonyl chloride, followed by dropwise addition of 0.90 g (8.9 mmol) of triethylamine. After the reaction mixture is stirred at 0° C. for 3 hours, it is poured into ice water, and extracted with ethyl acetate. The organic phase is washed with water and brine, dried over $MgSO_4$, and concentrated. The residue is purified by flash chromatography on silica gel with ethyl acetate and hexane (1:9) as an eluent, yielding 1.2 g (2.9 mmol; 49%) of 2,2,2-trifluoro-1-(2-methylphenyl)-ethanone oxime-O-(10-camphorylsulfonate) as a colorless liquid. The structure is confirmed by the $^1$H-NMR spectrum (CDCl$_3$). δ [ppm]: 0.92 (s, 3H), 1.12(Z)/1.18(E) (s, 3H), 1.38–1.50 (m, 1H), 1.55–1.75 (m, 1H), 1.90–2.18 (m, 3H), 2.28–2.53 (m, 1H), 3.84(Z)/3.90(E) (d, 1H), 7.15–7.46 (m, 4H). The $^1$H-NMR reveals that the product is a 7:3 mixture of Z and E isomers. The signals are tentatively assigned to the E- and Z-conformations.

EXAMPLE 10

2,2,2-Trifluoro-1-(2,4-dimethylphenyl)-ethanone oxime-O-(10-camphorylsulfonate)

10.1: 2,2,2-Trifluoro-1-(2,4-dimethylphenyl)-ethanone 30.4 g (0.286 mol) of m-xylene and 34.9 g (0.286 mol) of 4-dimethylaminopyridine are mixed in 400 ml of $CH_2Cl_2$ and cooled by ice bath. To the solution are added 87.6 g (0.657 mol) of $AlCl_3$, followed by dropwise addition of 60 g (0.286 mol) of trifluoroacetic anhydride. The reaction mixture is stirred at room temperature overnight, poured into ice water, and extracted with $CH_2Cl_2$. The organic phase is washed with water, $NaHCO_3$ aq, and brine, dried over $MgSO_4$, and concentrated. The residue is distilled at 100° C./15 mmHg, yielding 12.6 g of the crude product as colorless liquid. This crude product is used in the next reaction step without further purification.

10.2: 2,2,2-Trifluoro-1-(2,4-dimethylphenyl)-ethanone oxime 12.6 g (0.062 mol) of 2,2,2-trifluoro-1-(2,6-dimethylphenyl)-ethanone are dissolved in 30 ml of ethanol at 80° C. To the solution are added dropwise 4.6 g (0.066 mol) of hydroxylammonium chloride and 8.7 g (0.106 mol) of sodium acetate dissolved in 15 ml of water. The reaction mixture is refluxed overnight, affording white precipitation. The mixture is poured into ice water, and extracted with ethyl acetate. The organic phase is washed with water, $NH_4Cl$ aq, and brine, dried over $MgSO_4$, and concentrated, yielding 11.9 g of crude 2,2,2-trifluoro-1-(2,4-dimethylphenyl)-ethanone oxime as a colorless liquid. The crude product is used in the next reaction step without further purification.

10.3: 2,2,2-Trifluoro-1-(2,4-dimethylphenyl)-ethanone oxime-O-(10-camphorylsulfonate)

2.0 g (9.2 mmol) of 2,2,2-trifluoro-1-(2,4-dimethylphenyl)-ethanone oxime are dissolved in 20 ml of THF and cooled by ice bath. To the solution are added 2.5 g (10.1 mmol) of 10-camphorylsulfonyl chloride, followed by dropwise addition of 1.4 g (13.8 mmol) of triethylamine. The reaction mixture is stirred at 0° C. for 50 min, poured into ice water, and extracted with ethyl acetate. The organic phase is washed with water and brine, dried over $MgSO_4$, and concentrated. The residue is purified by flash chromatography on silica gel with ethyl acetate and hexane (3:7) as eluent, yielding 2.2 g (5.0 mmol; 54%) of 2,2,2-trifluoro-1-(2,4-dimethylphenyl)-ethanone oxime-O-(10-camphorylsulfonate) as a colorless liquid. The structure is confirmed by the $^1$H-NMR spectrum ($CDCl_3$). $\delta$ [ppm]: 0.92 (s, 3H), 1.12(Z)/1.18(E) (s, 3H), 1.38–1.50 (m, 1H), 1.54–1.80 (m, 1H), 1.90–2.58 (m, 11H), 3.25–3.38 (m, 1H), 3.83(Z)/3.88(E) (d, 1H), 7.03–7.28 (m, 3H). The $^1$H-NMR reveals that the product is a 3:2 mixture of Z and E isomers. The signals are tentatively assigned to the E- and Z-conformations.

EXAMPLE 11

2,2,2-Trifluoro-1-(2,4-dimethylphenyl)-ethanone oxime-O-(1-naphthylsulfonate)

2.0 g (9.2 mmol) of 2,2,2-trifluoro-1-(2,4-dimethylphenyl)-ethanone oxime (prepared as described in example 10.2) are dissolved in 30 ml of THF and cooled by ice bath. To the solution are added 2.3 g (10.1 mmol) of 1-naphthylsulfonyl chloride, followed by dropwise addition of 1.4 g (13.8 mmol) of triethylamine. After the reaction mixture is stirred at 0° C. for 60 min, it is poured into ice water, and extracted with ethyl acetate. The organic phase is washed with water and brine, dried over $MgSO_4$, and concentrated. The residue is purified by flash chromatography on silica gel with ethyl acetate and hexane (3:7) as eluent, yielding 3.0 g (7.3 mmol; 80%) of 2,2,2-trifluoro-1-(2,4-dimethylphenyl)-ethanone oxime-O-(1-naphthylsulfonate) as white solid, mp. 85–124° C. The structure is confirmed by the $^1$H-NMR spectrum ($CDCl_3$). $\delta$ [ppm]: 1.71(E)/2.03(Z) (s, 3H), 2.28(E)/2.39(Z) (s, 3H), 6.77–7.13 (m, 3H), 7.54–7.78 (m, 3H), 7.95–8.03 (m, 1H), 8.15–8.23 (m, 1H), 8.35–8.70 (m, 2H). The $^1$H-MNR reveals that the product is a 7:3 mixture of Z and E isomers. The signals are tentatively assigned to the E- and Z-conformations.

EXAMPLE 12

2,2,2-Trifluoro-1-(2,4-dimethylphenyl)-ethanone oxime-O-(2-naphthylsulfonate)

2.0 g (9.2 mmol) of 2,2,2-trifluoro-1-(2,4-dimethylphenyl)-ethanone oxime (prepared as described in example 10.2) are dissolved in 30 ml of THF and cooled by an ice bath. To the solution are added 2.3 g (10.1 mmol) of 2-naphthylsulfonyl chloride, followed by dropwise addition of 1.4 g (13.8 mmol) of triethylamine. The reaction mixture is stirred at 0° C. for 60 min, poured into ice water, and extracted with ethyl acetate. The organic phase is washed with water and brine, dried over $MgSO_4$, and concentrated. The residue is purified by flash chromatography on silica gel with ethyl acetate and hexane (3:7) as an eluent, yielding 2.1 g (5.3 mmol; 57%) of 2,2,2-trifluoro-1-(2,4-dimethylphenyl)-ethanone oxime-O-(2-naphthylsulfonate) as a colorless liquid. The structure is confirmed by the $^1$H-NMR spectrum ($CDCl_3$). $\delta$ [ppm]: 2.05(E)/2.10(Z) (s, 3H), 2.31(E)/2.35(Z) (s, 3H), 6.92–7.13 (m, 3H), 7.61–7.77 (m, 2H), 7.88–8.08 (m, 4H), 8.61 (s, 1H). The $^1$H-NMR reveals that the product is a 7:3 mixture of Z and E isomers. The signals are tentatively assigned to the E- and Z-conformations.

EXAMPLE 13

2,2,2-Trifluoro-1-(2,4,6-trimethylphenyl)-ethanone oxime-O-(10-camphorylsulfonate)

13.1: 2,2,2-Trifluoro-1-(2,4,6-trimethylphenyl)-ethanone 50.0 g (0.416 mol) of mesitylene and 50.8 g (0.416 mol) of 4-dimethylaminopyridine are mixed in 600 ml of $CH_2Cl_2$ and cooled in an ice bath. To the solution are added dropwise 87.4 g (0.416 mol) of trifluoroacetic anhydride, followed by 128 g (0.957 mol) of $AlCl_3$ by portions. The reaction mixture is stirred at room temperature overnight, poured into ice water, and extracted with $CH_2Cl_2$. The organic phase is washed with water, dried over $MgSO_4$, and concentrated. The residue is distilled at 100° C./1 mm Hg, yielding 44.6 g of the crude product as a colorless liquid. The crude product is used in the next step without further purification.

13.2: 2,2,2-Trifluoro-1-(2,4,6-trimethylphenyl)-ethanone oxime 6.3 g (0.029 mol) of 2,2,2-trifluoro-1-(2,4,6-trimethylphenyl)-ethanone are dissolved in 30 ml of ethanol at 80° C. To the solution are added dropwise 2.0 g (0.029 mol) of hydroxylammonium chloride and 4.1 g (0.050 mol) of sodium acetate dissolved in 15 ml of water. The reaction mixture is refluxed overnight, poured into ice water, and extracted with ethyl acetate. The organic phase is washed with brine, dried over $MgSO_4$, and concentrated. The residue is purified by recrystallization from 20 ml of hexane, yielding 1.9 g of 2,2,2-trifluoro-1-(2,4,6-trimethylphenyl)-ethanone oxime in the form of white crystals, mp. 119–125° C.

13.3: 2,2,2-Trifluoro-1-(2,4,6-trimethylphenyl)-ethanone oxime-O-(10-camphorylsulfonate)

1.8 g (7.8 mmol) of 2,2,2-trifluoro-1-(2,4,6-trimethylphenyl)-ethanone oxime are dissolved in 20 ml of THF and cooled by an ice bath. To the solution are added 2.2 g (8.6 mmol) of 10-camphorsulfonyl chloride, followed by dropwise addition of 1.2 g (11.7 mmol) of triethylamine. The reaction mixture is stirred at 0° C. for 50 min, poured into ice water, and extracted with ethyl acetate. The organic phase is washed with water and brine, dried over $MgSO_4$, and concentrated. The residue is purified by flash chromatography on silica gel with ethyl acetate and hexane (1:4) as eluent, yielding 3.4 g (7.6 mmol; 97%) of 2,2,2-trifluoro-1-(2,4,6-trimethylphenyl)-ethanone oxime-O-(10-camphorylsulfonate) as a colorless liquid. The structure is confirmed by the $^1$H-NMR spectrum ($CDCl_3$). $\delta$ [ppm]: 0.92 (s, 3H), 1.14 (s, 3H), 1.40–1.49 (m, 1H), 1.65–1.75 (m, 1H), 1.93–2.47 (m, 14H), 3.35 (d, 1H), 3.84 (d, 1H), 7.12 (s, 2H).

EXAMPLE 14

2,2,2-Trifluoro-1-(2,4,6-trimethylphenyl)-ethanone oxime-O-(1-naphthylsulfonate)

2.0 g (8.7 mmol) of 2,2,2-trifluoro-1-(2,4,6-trimethylphenyl)-ethanone oxime (prepared as described in example 13.2) are dissolved in 40 ml of THF and cooled in an ice bath. To the solution are added 2.2 g (9.5 mmol) of 1-naphthylsulfonyl chloride, followed by dropwise addition of 1.3 g (13.0 mmol) of triethylamine. The reaction mixture is stirred at 0° C. for 150 min, poured into ice water, and extracted with ethyl acetate. The organic phase is washed with water and brine, dried over $MgSO_4$, and concentrated. The residue is purified by recrystallization from 5 ml of methanol, yielding 1.5 g (3.6 mmol; 41%) of 2,2,2-trifluoro-1-(2,4,6-trimethylphenyl)-ethanone oxime-O-(1-naphthylsulfonate) as a white solid, mp. 137–145° C. The structure is confirmed by the $^1$H-NMR spectrum ($CDCl_3$). δ [ppm]: 1.88–2.39 (m, 9H), 6.49–7.12 (m, 2H), 7.56–7.72 (m, 3H), 8.00 (t, 1H), 8.22 (d, 1H), 8.37–8.54 (m, 2H).

EXAMPLE 15

2,2,2-Trifluoro-1-(2,4,6-trimethylphenyl)-ethanone oxime-O-(2-naphthylsulfonate)

2.0 g (8.7 mmol) of 2,2,2-trifluoro-1-(2,4,6-trimethylphenyl)-ethanone oxime (prepared as described in example 13.2) are dissolved in 50 ml of THF and cooled by an ice bath. To the solution are added 2.2 g (9.5 mmol) of 2-naphthylsulfonyl chloride, followed by dropwise addition of 1.4 g (14.3 mmol) of triethylamine. The reaction mixture is stirred at 0° C. for 210 min, poured into ice water, and extracted with ethyl acetate. The organic phase is washed with water and brine, dried over $MgSO_4$, and concentrated. The residue is purified by recrystallization from hexane and ethyl acetate solution (9:1), yielding 1.5 g (3.6 mmol; 41%) of 2,2,2-trifluoro-1-(2,4,6-trimethylphenyl)-ethanone oxime-O-(2-naphthylsulfonate) as a white solid, mp. 106–113° C. The structure is confirmed by the $^1$H-NMR spectrum ($CDCl_3$). δ [ppm]: 2.21 (s, 3H), 2.30 (s, 6H), 7.01 (s, 2H), 7.63–7.76 (m, 2H), 7.96 (t, 2H), 8.03 (d, 2H), 8.62 (s, 1H).

EXAMPLE 16

2,2,2-Trifluoro-1-(4-methoxyphenyl)-ethanone oxime-O-methylsulfonate 16.1: 2,2,2-Trifluoro-1-(4-methoxyphenyl)-ethanone 29.0 g (0.268 mol) of anisole and 32.8 g (0.268 mol) of 4-dimethylaminopyridine are mixed in 300 ml of $CH_2Cl_2$ and cooled by an ice bath. To the solution are added dropwise 56.3 g (0.268 mol) of trifluoroacetic anhydride, followed by 82.2 g (0.616 mol) of $AlCl_3$ by portions. The reaction mixture is stirred at room temperature overnight, poured into ice water, and extracted with $CH_2Cl_2$. The organic phase is washed with water, dried over $MgSO_4$, and concentrated. The residue is purified by flash chromatography on silica gel with ethyl acetate and hexane (5:95), yielding 37.8 g of the product as a brownish liquid.

16.2: 2,2,2-Trifluoro-1-(4-methoxyphenyl)-ethanone oxime 37.2 g (0.182 mol) of 2,2,2-trifluoro-1-(4-methoxyphenyl)-ethanone are dissolved in 150 ml of ethanol at 80° C. To the solution are added dropwise 13.3 g (0.191 mol) of hydroxylammonium chloride and 25.4 g (0.309 mol) of sodium acetate dissolved in 75 ml of water. The reaction mixture is refluxed for 4 hours. The mixture is poured into ice water, the precipitate is filtered, yielding 30.0 g of 2,2,2-trifluoro-1-(4-methoxyphenyl)-ethanone oxime as a pale yellow solid. The crude product is used in the next reaction step without further purification.

16.3: 2,2,2-Trifluoro-1-(4-methoxyphenyl)-ethanone oxime-O-(methylsulfonate)

6.5 g (30.0 mmol) of 2,2,2-trifluoro-1-(4-methoxyphenyl)-ethanone oxime are dissolved in 25 ml of THF and cooled in an ice bath. To the solution are added 3.8 g (33.0 mmol) of methanesulfonyl chloride, followed by dropwise addition of 4.6 g (45.0 mmol) of triethylamine. The reaction mixture is stirred at 0° C. for 5 hours, poured into ice water, and extracted with ethyl acetate. The organic phase is washed with water and brine, dried over $MgSO_4$, and concentrated. The residue is purified by recrystallization from 15 ml of ethanol, yielding 5.9 g (20.0 mmol; 67%) of 2,2,2-trifluoro-1-(4-methoxyphenyl)-ethanone oxime-O-(methylsulfonate) as a white solid, mp. 47–51° C. The structure is confirmed by the $^1$H-NMR spectrum ($CDCl_3$). δ [ppm]: 3.27 (s, 3H), 3.88 (s, 3H), 7.00 (d, 2H), 7.55 (d, 2H).

EXAMPLE 17

2,2,2-Trifluoro-1-(4-methylthiophenyl)-ethanone oxime-O-methylsulfonate 17.1: 2,2,2-Trifluoro-1-(4-methylthiophenyl)-ethanone 50.0 g (0.403 mol) of thioanisole and 49.2 g (0.403 mol) of 4-dimethylaminopyridine are mixed in 500 ml of $CH_2Cl_2$ and cooled in an ice bath. To the solution are added dropwise 84.6 g (0.403 mol) of trifluoroacetic anhydride, followed by 123.0 g (0.926 mol) of $AlCl_3$ by portions. The reaction mixture is stirred at room temperature overnight, poured into ice water, and extracted with $CH_2Cl_2$. The organic phase is washed with water, dried over $MgSO_4$, and concentrated, yielding 50.0 g of 2,2,2-trifluoro-1-(4-methylthiophenyl)-ethanone as a yellow solid. The crude product is used in the next reaction step without further purification.

17.2: 2,2,2-Trifluoro-1-(4-methylthiophenyl)-ethanone oxime 49.3 g (0.224 mol) of 2,2,2-trifluoro-1-(4-methylthiophenyl)-ethanone are dissolved in 250 ml of ethanol at 80° C. To the solution are added dropwise 16.3 g (0.235 mol) of hydroxylammonium chloride and 31.2 g (0.381 mol) of sodium acetate dissolved in 125 ml of water. The reaction mixture is refluxed for 6.5 hours, and poured into ice water. Filtration of the precipitate yields 51.1 g of 2,2,2-trifluoro-1-(4-methylthiophenyl)-ethanone oxime, as a yellow solid. The crude product is used in the next reaction step without further purification.

17.3: 2,2,2-Trifluoro-1-(4-methylthiophenyl)-ethanone oxime-O-(methylsulfonate)

5.9 g (25.0 mmol) of 2,2,2-trifluoro-1-(4-methylthiophenyl)-ethanone oxime are dissolved in 30 ml of THF and cooled by an ice bath. To the solution are added 3.2 g (28.0 mmol) of methylsulfonyl chloride, followed by dropwise addition of 3.8 g (38.0 mmol) of triethylamine. The reaction mixture is stirred at 0° C. for 5 hours, poured into ice water, and extracted with ethyl acetate. The organic phase is washed with water and brine, dried over $MgSO_4$, and concentrated. The residue is purified by recrystallization from 30 ml of ethanol, yielding 3.9 g (12.4 mmol; 50%) of 2,2,2-trifluoro-1-(4-methylthiophenyl)-ethanone oxime-O-(methylsulfonate) as a pale yellowish solid, mp. 87–90° C. The structure is confirmed by the $^1$H-NMR spectrum ($CDCl_3$). δ [ppm]: 2.52 (s, 3H), 3.26 (s, 3H), 7.31 (d, 2H), 7.47 (d, 2H).

EXAMPLE 18

2,2,2-Trifluoro-1-(3,4-dimethoxyphenyl)-ethanone oxime-O-methylsulfonate 18.1: 2,2,2-Trifluoro-1-(3,4-dimethoxyphenyl)-ethanone 13.8 g (0.10 mol) of 1,2-dimethoxybenzene and 12.2 g (0.10 mol) of 4-dimethylaminopyridine are mixed in 75 ml of $CH_2Cl_2$ and cooled in an ice bath. To the solution are added dropwise 21.0 g (0.10 mol) of trifluoroacetic anhydride, followed by 32.0 g (0.24 mol) of $AlCl_3$ by portions. The reaction mixture is stirred at room temperature overnight, poured into ice water, and extracted with $CH_2Cl_2$. The organic phase is washed with water, dried over $MgSO_4$, and concentrated. The residue is purified by flash chromatography on silica gel with ethyl acetate and hexane (1:9), yielding 2.9 g of product as white solid.

18.2: 2,2,2-Trifluoro-1-(3,4-dimethoxyphenyl)-ethanone oxime 2.9 g (9.7 mmol) of 2,2,2-trifluoro-1-(3,4-dimethoxyphenyl)-ethanone are dissolved in 12 ml of ethanol at 80° C. To the solution are added dropwise 0.83 g (12.0 mmol) of hydroxylammonium chloride and 1.2 g (15.0 mmol) of sodium acetate dissolved in 6 ml of water. The reaction mixture is refluxed for 7.5 hours, poured into ice water, and extracted with ether. The organic phase is washed with water and brine, dried over $MgSO_4$, and concentrated, yielding 2.3 g of 2,2,2-trifluoro-1-(3,4-dimethoxyphenyl)-ethanone oxime. The crude product is used in the next reaction step without further purification.

18.3: 2,2,2-Trifluoro-1-(3,4-dimethoxyphenyl)-ethanone oxime-O-methylsulfonate 2.3 g (9.0 mmol) of 2,2,2-trifluoro-1-(3,4-dimethoxyphenyl)-ethanone oxime are dissolved in 20 ml of THF and cooled in an ice bath. To the solution are added 1.2 g (10.0 mmol) of methylsulfonyl chloride, followed by dropwise addition of 1.5 g (15.0 mmol) of triethylamine. The reaction mixture is stirred at 0° C. for 5 hours, poured into ice water, and extracted with ethyl acetate. The organic phase is washed with water and brine, dried over $MgSO_4$, and concentrated. The residue is purified by recrystallization from 15 ml of ethanol, yielding 2.2 g (6.7 mmol; 74%) of 2,2,2-trifluoro-1-(3,4-dimethoxyphenyl)-ethanone oxime-O-(methylsulfonate) as a white solid, mp. 105–107° C. The structure is confirmed by the $^1$H-NMR spectrum ($CDCl_3$). δ [ppm]: 3.27 (s, 3H), 3.91 (s, 3H), 3.95 (s, 3H), 6.96 (d, 1H), 7.05 (s, 1H), 7.20 (d, 1H).

EXAMPLE 19

2,2,3,3,4,4,4-Heptafluoro-1-phenyl-butanone oxime-O-(10-camphorylsulfonate)

19.1: 2,2,3,3,4,4,4-Heptafluoro-1-phenyl-butanone oxime 10 g (0.037 mol) of 2,2,3,3,4,4,4-heptafluoro-1-phenyl-butanone are dissolved in 30 ml of ethanol at 80° C. To the solution are added dropwise 2.6 g (0.038 mol) of hydroxylammonium chloride and 5.1 g (0.062 mol) of sodium acetate dissolved in 15 ml of water. The reaction mixture is refluxed for 6 hours. The mixture is poured into ice water, and extracted with ethyl acetate. The organic phase is washed with brine, dried over $MgSO_4$, and concentrated. The residue is purified by recrystallization from 5 ml of hexane, yielding 4.7 g of 2,2,3,3,4,4,4-heptafluoro-1-phenyl-butanone oxime as a white solid, mp. 57–60° C.

19.2: 2,2,3,3,4,4,4-Heptafluoro-1-phenyl-butanone oxime-O-(10-camphorylsulfonate)

2.0 g (10.6 mmol) of 2,2,3,3,4,4,4-heptafluoro-1-phenyl-butanone oxime are dissolved in 40 ml of THF and cooled in an ice bath. To the solution are added 2.9 g (11.6 mmol) of 10-camphorylsulfonyl chloride, followed by dropwise addition of 1.6 g (16.0 mmol) of triethylamine. The reaction mixture is stirred at 0° C. for 4.5 hours, poured into ice water, and extracted with ethyl acetate. The organic phase is washed with water and brine, dried over $MgSO_4$, and concentrated. The residue is purified by flash chromatography on silica gel with ethyl acetate and hexane (1:9) as eluent, yielding 2.3 g (4.6 mmol; 43%) of 2,2,3,3,4,4,4-heptafluoro-1-phenyl-butanone oxime-O-(10-camphorylsulfonate) as a pale yellow liquid The structure is confirmed by the $^1$H-NMR spectrum ($CDCl_3$). δ [ppm]: 0.92 (s, 3H), 1.12(Z)/1.18(E) (s, 3H), 1.40–1.50 (m, 1H), 1.66–1.73 (m, 1H), 1.92–2.18 (m, 3H), 2.31–2.54 (m, 2H), 3.28(Z)/3.33(E) (d, 1H), 3.83(Z)/3.93(E) (d, 1H), 7.37–7.63 (m, 5H). The $^1$H-NMR reveals that the product is a 3:2 mixture of Z and E isomers. The signals are tentatively assigned to the E- and Z-conformations.

EXAMPLES 20–36

The compounds of examples 20 to 36 are obtained according to the method described in example 1.2, using the corresponding educts. The structures and physical data are listed in table 1.

TABLE 1

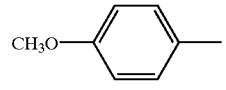

| | Structure | | | State: mp(° C.)/ |
|---|---|---|---|---|
| Ex. | $R_A$ | $R_B$ | Purification | $^1$H-NMR [δ(ppm)] |
| 20 | 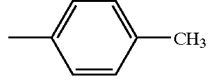 | 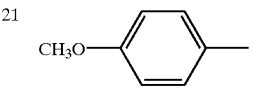 | recrystallization from ethanol | white solid, 112–115/ 2.48(s, 3H), 3.87(s, 3H), 6.97(d, 2H), 7.38(d, 2H), 7.46(d, 2H), 7.90(d, 2H) |
| 21 | 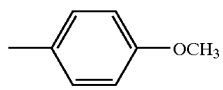 | | recrystallization from methanol | white solid, 94–97/ 3.85(s, 3H), 3.90(s, 3H), 6.97(d, 2H), 7.03(d, 2H), 7.46(d, 2H), 7.95(d, 2H) |

TABLE 1-continued $$\underset{F_3C}{\overset{R_A}{>}}C=N-O-\underset{O}{\overset{O}{\underset{\|}{S}}}-R_B$$

| Ex. | $R_A$ | $R_B$ | Purification | State: mp(° C.)/ $^1$H-NMR [δ(ppm)] |
|---|---|---|---|---|
| 22 | CH₃O—C₆H₄— | —C₆H₄—C₁₂H₂₅ | chromatography (hexane:ethyl acetate = 95:5) | pale yellow liquid/ 0.73–1.79(m, 23H), 2.48–2.85(m, 2H), 3.85(s, 3H), 6.97 (d, 2H), 7.30–7.39(m, 2H), 7.45(d, 2H), 7.88–7.95(m, 2H) |
| 23 | CH₃O—C₆H₄— | —C₈H₁₇ | chromatography (hexane:ethyl acetate = 9:1) | pale yellow liquid/ 0.87(t, 3H), 1.21–1.52(m, 10H), 1.82–1.92(m, 2H), 3.39(t, 2H), 3.37(s, 3H), 6.99(d, 2H), 7.54(d, 2H) |
| 24 | CH₃S—C₆H₄— | —C₆H₄—OCH₃ | recrystallization from hexane/ethyl acetate | white solid, 85–86/ 2.51(s, 3H), 3.91(s, 3H), 7.04(d, 2H), 7.28(d, 2H), 7.37(d, 2H), 7.95(d, 2H) |
| 25 | CH₃S—C₆H₄— | —C₆H₄—C₁₂H₂₅ | chromatography (hexane:ethyl acetate = 95:5) | yellow liquid/ 0.75–1.78(m, 23H), 2.52(E) (s, 3H), 2.54–2.85(m, 2H), 7.02–7.43(m, 6H), 7.88–7.95(m, 2H) |
| 26 | CH₃S—C₆H₄— | —C₈H₁₇ | chromatography (hexane:ethyl acetate = 95:5) | white solid, 40–41/0.82(t, 3H), 1.13–1.31(m, 8H), 1.33–1.43(m, 2H), 1.74–1.84(m, 2H), 2.45(s, 3H), 3.33(t, 2H), 7.24(d, 2H), 7.38(d, 2H) |
| 27 | CH₃S—C₆H₄— | 2-naphthyl | recrystallization from toluene | white solid, 122–128/ 2.52(s, 3H), 7.28(d, 2H), 7.37(d, 2H), 7.65–7.77(m, 2H), 7.92–8.07(m, 4H), 8.62(s, 1H) |
| 28 | 2-CH₃—C₆H₄— | —CH₃ | chromatography (hexane:ethyl acetate = 4:1) | white solid, 58–60/ 2.19(E)/2.38(Z) (s, 3H), 3.25(s, 3H), 7.17–7.47(m, 4H). Z:E = 1:1 |
| 29 | 4-CH₃—C₆H₄— | —C₆H₅ | recrystallization from ethanol | white solid, 63–75/ 2.40(s, 3H), 7.20–7.35(m, 4H), 7.53–7.76(m, 3H), 8.03 (d, 2H) |
| 30 | 4-Cl—C₆H₄— | —C₆H₅ | chromatography (hexane:ethyl acetate = 9:1) | white solid, 68–76/ 7.33–7.78(m, 7H), 7.97–8.08(m, 2H) |
| 31 | mixture of α- and β-naphthyl | —CH₃ | chromatography (hexane:ethyl acetate = 5:1) | brownish yellow solid, 55–57/ 3.25/3.27/3.30(s,3H), 7.47–8.05(m,7H); mixture of α-, β-, E-, Z-isomers |

TABLE 1-continued

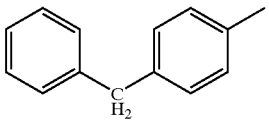

| Ex. | R_A | R_B | Purification | State: mp(° C.)/ $^1$H-NMR [δ(ppm)] |
|---|---|---|---|---|
| 32 | (4-benzylphenyl) | —CH$_3$ | chromatography (hexane:ethyl acetate = 5:1) | yellow oil/ 3.24(s, 3H), 4.04(s, 2H), 7.19(m, 9H) |
| 33 | PhO—(CH$_2$)$_2$—O—(4-C$_6$H$_4$) | —CH$_3$ | chromatography CH$_2$Cl$_2$ | white solid, 92–96/ 3.24(s, 3H), 4.31–4.40(m, 4H), 6.92–7.07(m, 5H), 7.28–7.33(m, 2H), 7.51–7.61(m, 2H) |
| 34 | mixture of α- and β-naphthyl | —C$_3$H$_7$ | chromatography (hexane:ethyl acetate = 5:1) | yellow oil/ 1.11(t, 3H), 1.99(m, 2H), 3.39(t, 2H), 7.44–8.02(m, 7H); mixture of α-, β-, E-, Z-isomers |
| 35 | (4-benzylphenyl) | —C$_3$H$_7$ | chromatography (hexane:ethyl acetate = 5:1) | yellow oil/ 1.08(t, 3H), 1.90(m, 2H), 3.39(t, 2H), 7.19–7.43(m, 9H) |
| 36 | H$_3$C—SO$_2$—(4-C$_6$H$_4$) | —C$_3$H$_7$ | precipitation with C$_2$H$_5$OH/H$_2$O | white solid, 130 |

EXAMPLE 37

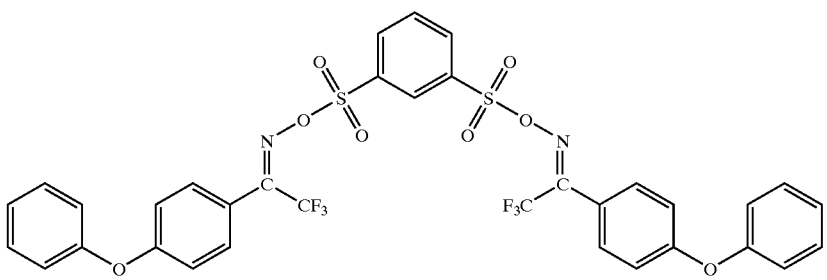

Compound of formula III, R$_1$ is

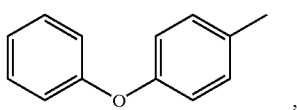

,

R$_2$ is F; R$_3$' is

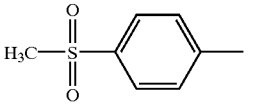

The compound of example 37 is prepared by reacting 2 moles of the corresponding oxime with one mole of the corresponding dichloride according to the method described in example 1.2. The compound is a white solid with a melting point of 111–112° C. $^1$H-NMR data [ppm]: 7.00–7.13 (m, 8H), 7.20–7.28 (m, 2H), 7.38–7.48 (m, 8H), 7.87 (t, 1H), 8.36 (d, 2H), 8.63 (s, 1H).

EXAMPLE 38

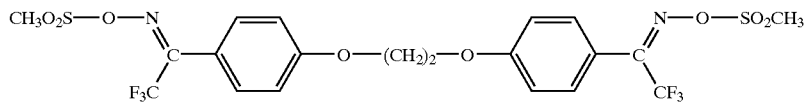

Compound of formula II; $R_1'$ is

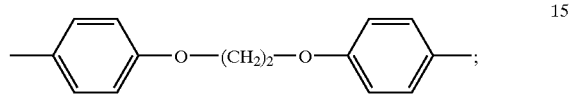

$R_2$ is F; $R_3$ is —SO$_2$CH$_3$

The compound of example 38 is prepared by reacting 1 mole of the corresponding bisoxime with 2 moles of the corresponding chloride according to the method described in example 1.2. The compound is isolated by chromatography with hexane:ethyl acetate (5:1) and is a pale yellow liquid. $^1$H-NMR data [ppm]: 3.25/3.27 (s, 6H), 4.43 (s, 4H), 7.02–7.08 (m, 4H), 7.53–7.62 (m, 4H).

EXAMPLE 39

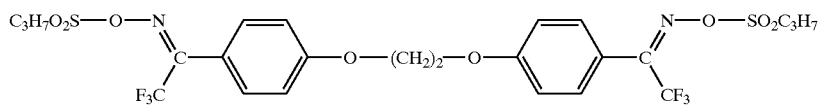

Compound of formula II; $R_1'$ is

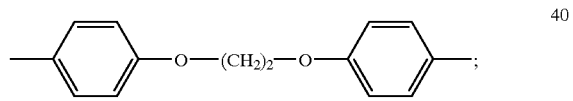

$R_2$ is F; $R_3$ is —SO$_2$C$_3$H$_7$

The compound of example 39 is prepared as described in example 38. The compound is isolated by chromatography with hexane:ethyl acetate (5:1) and is an orange liquid. $^1$H-NMR data [ppm]: 1.12 (t,6H), 1.88–2.02 (m, 4H), 3.34–3.43 (m, 4H), 4.43 (s, 4H), 7.00–7.07 (m, 4H), 7.51–7.61 (m, 4H).

EXAMPLES 40–74

The compounds of examples 40 to 74 are obtained according to the method described in example 1.2, using the corresponding educts. The structures and physical data are listed in table 2.

TABLE 2

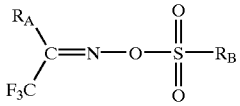

| Ex. | $R_A$ | $R_B$ | Purification | State: mp(° C.)/ $^1$H-NMR [δ(ppm)] |
|---|---|---|---|---|
| 40 | CH₃S—C₆H₄— | 2,4,6-trimethylphenyl | recrystallization from methanol/ethyl acetate | white solid, 126–127/ 2.34(s, 3H), 2.52(s, 3H), 2.60(s, 6H), 7.04(s, 2H), 7.29(d, 2H), 7.38(d, 2H) |
| 41 | CH₃O—C₆H₄— | 2,4,6-trimethylphenyl | recrystallization from methanol | white solid, 101–102/ 2.34(s, 3H), 2.60(s, 6H), 3.87(s, 3H), 6.96–7.03(m, 4H), 7.46(d, 2H) |
| 42 | PhO—C₆H₄— | —CH₃ | chromatography (hexane:ethyl acetate = 4:1) | white solid, 71–73/ 3.26(s, 3H), 7.06(d, 2H), 7.11(d, 2H), 7.24(t, 1H), 7.43(t, 2H), 7.53(d, 2H) |
| 43 | CH₃S—C₆H₄— | camphor-CH₂— | chromatography (hexane:ethyl acetate = 85:15) | pale yellow liquid/0.93(t, 3H), 1.13(s, 3H), 1.40–1.48(m, 1H), 1.67–1.75(m, 1H), 1.93–2.18(m, 3H), 2.33–2.46(m, 2H), 2.52(s, 3H), 3.34(d, 1H), 3.85(d, 1H), 7.32(d, 2H), 7.47(d, 2H) |
| 44 | CH₃O—C₆H₄— | 2-naphthyl (methyl-substituted) | recrystallization from methanol | white solid, 85–87/ 3.87(s, 3H), 6.98(d, 2H), 7.46(d, 2H), 7.63–7.76(m, 2H), 7.93–8.00(m, 2H), 8.03(d, 2H), 8.63(s, 1H) |
| 45 | CH₃O—C₆H₄— | camphor-CH₂— | chromatography (hexane:ethyl acetate = 3:1) | colorless liquid/ 0.93(s, 3H), 1.14(s, 3H), 1.40–1.49(m, 1H), 1.68–1.77(m, 1H), 1.93–2.18(m, 3H), 2.35–2.46(m, 2H), 3.35(d, 1H), 3.85(d, 1H), 3.88(s, 3H), 7.00(d, 2H), 7.54(d, 2H) |
| 46 | CH₃O—C₆H₄— | PhCH₂— | recrystallization from hexane/ethyl acetate | white solid, 81–82/ 3.84(s, 3H), 4.68(s, 2H), 6.93(d, 2H), 7.36(d, 2H), 7.42(s, 5H) |

TABLE 2-continued $$\underset{F_3C}{\overset{R_A}{>}}C=N-O-\underset{O}{\overset{O}{\underset{\|}{S}}}-R_B$$

| Ex. | Structure $R_A$ | $R_B$ | Purification | State: mp(° C.)/ $^1$H-NMR [δ(ppm)] |
|---|---|---|---|---|
| 47 | CH$_3$O—C$_6$H$_4$— | 2,4,6-triisopropylphenyl (with methyl) | recrystallization from hexane | white solid, 87–88/ 1.21(d, 12H), 1.28(d, 6H), 2.93(m, 1H), 3.88(s, 3H), 4.06(m, 2H), 6.98(d, 2H), 7.19(s, 2H), 7.49(d, 2H) |
| 48 | C$_6$H$_5$—O—C$_6$H$_4$— | 2,4,6-trimethylphenyl | recrystallization from hexane | white solid, 78–80/ 2.35(s, 3H), 2.60(s, 6H), 6.98–7.07(m, 4H), 7.10(d, 2H), 7.23(t, 1H), 7.39–7.47(m, 4H) |
| 49 | CH$_3$O—C$_6$H$_4$— | —CH(CH$_3$)$_2$ | chromatography (hexane:ethyl acetate = 5:1) | pale yellow liquid/ 1.47(d, 6H), 3.81(m, 1H), 3.87(s, 3H), 7.00(d, 2H), 7.53(d, 2H) |
| 50 | CH$_3$S—C$_6$H$_4$— | —C$_3$H$_7$ | chromatography (hexane:ethyl acetate = 5:1) | white solid, 69–70/ 1.12(t, 3H), 1.94(m, 2H), 2.53(s, 3H), 3.39(t, 2H), 7.30(d, 2H), 7.45(d, 2H) |
| 51 | CH$_3$S—C$_6$H$_4$— | —CH(CH$_3$)$_2$ | recrystallization from hexane/ethyl acetate | white solid, 51–52/ 1.47(d, 6H), 2.52(s, 3H), 3.80(m, 1H), 7.32(d, 2H), 7.46(d, 2H) |
| 52 | CH$_3$S—C$_6$H$_4$— | —C$_4$H$_9$ | chromatography (hexane:ethyl acetate = 5:1) | colorless liquid/ 0.96(t, 3H), 1.49(m, 2H), 1.87(m, 2H), 2.53(s, 3H), 3.40(t, 2H), 7.32(d, 2H), 7.46(d, 2H) |
| 53 | CH$_3$O—C$_6$H$_4$— | —C$_4$H$_9$ | chromatography (hexane:ethyl acetate = 5:1) | brownish yellow liquid/ 0.97(t, 3H), 1.50(m, 2H), 1.87(m, 2H), 3.42(t, 2H), 3.87(s, 3H), 7.00(d, 2H), 7.54(d, 2H) |
| 54 | C$_6$H$_5$—O—C$_6$H$_4$— | CH$_3$O—C$_6$H$_4$— | chromatography (hexane:ethyl acetate = 5:1) | white solid, 90–91/ 3.93(s, 3H), 6.98–7.12(m, 6H), 7.22(t, 1H), 7.38–7.46(m, 4H), 7.95(d, 2H) |
| 55 | C$_6$H$_5$—O—C$_6$H$_4$— | 2-naphthyl | recrystallization from 2-propanol | white solid, 147–148/ 7.03(d, 2H); 7.09(d, 2H), 7.21(t, 1H), 7.38–7.45(m, 4H), 7.63–7.77(m, 2H), 7.92–8.04(m, 4H), 8.63(s, 1H) |

TABLE 2-continued $$R_A \diagdown C = N - O - \underset{\underset{O}{\overset{O}{\|}}}{\overset{\|}{S}} - R_B$$
$$F_3C \diagup$$

| | Structure | | | State: mp(° C.)/ |
|---|---|---|---|---|
| Ex. | $R_A$ | $R_B$ | Purification | $^1$H-NMR [δ(ppm)] |
| 56 | Ph—O—C$_6$H$_4$— | —C$_8$H$_{17}$ | chromatography (hexane:ethyl acetate = 9:1) | brown liquid/0.84–0.93(m, 3H), 1.20–1.40(m, 8H), 1.40–1.54(m, 2H), 1.88(Z)/2.05(E)(m, 2H), 3.42(Z)/3.65(E) (t, 2H), 7.00–7.12(m, 4H), 7.22(t, 1H), 7.40(t, 2H), 7.50(d, 2H). E:Z = 1:3 The signals are tentatively assigned to E- and Z- isomers. |
| 57 | Ph—O—C$_6$H$_4$— | 2,4,6-triisopropylphenyl | chromatography (hexane:ethyl acetate = 6:1) | white solid, 70–72/ 1.17–1.30(m, 18H), 2.93(m, 1H), 4.05(m, 2H), 6.98–7.12(m, 4H), 7.15–7.27(m, 3H), 7.37–7.48(m, 4H) |
| 58 | Ph—O—C$_6$H$_4$— | —CH(CH$_3$)$_2$ | chromatography (hexane:ethyl acetate = 5:1) | white solid, 67–68/ 1.48(d, 6H), 3.82(m, 1H), 6.98–7.12(m, 4H), 7.22(t, 1H), 7.43(t, 2H), 7.50(d, 2H) |
| 59 | Ph—O—C$_6$H$_4$— | —C$_4$H$_9$ | chromatography (hexane:ethyl acetate = 8:1) | colorless liquid/0.98(t, 3H), 1.50(m, 2H), 1.88(m, 2H), 3.41(t, 2H), 7.00–7.14(m, 4H), 7.22(t, 1H), 7.42(t, 2H), 7.51(d, 2H) |
| 60 | Ph—S—C$_6$H$_4$— | —CH$_3$ | chromatography (hexane:methylene chloride = 1:1) | white solid, 101–103/ 3.25(s, 3H), 7.23(d, 2H), 7.37–7.58(m, 7H) |
| 61 | C$_8$H$_{17}$O—C$_6$H$_4$— | —CH$_3$ | chromatography (hexane:ethyl acetate = 5:1) | white solid, 54–55/0.90(t, 3H), 1.22–1.40(m, 8H), 1.40–1.52(m, 2H), 1.83(m, 2H), 3.27(s, 3H), 4.00(t, 2H), 6.98(d, 2H), 7.54(d, 2H) |
| 62 | Ph—CH$_2$—C$_6$H$_4$— | —CH$_3$ | chromatography (hexane:ethyl acetate = 6:1) | yellow liquid/3.25(s, 3H), 4.05(s, 2H), 7.18–7.35(m, 7H), 7.45(d, 2H) |
| 63 | C$_8$H$_{17}$O—C$_6$H$_4$— | —C$_3$H$_7$ | chromatography (hexane:ethyl acetate = 9:1) | colorless liquid/0.89(t, 3H), 1.11(t, 3H), 1.24–1.40(m, 8H), 1.41–1.52(m, 2H), 1.80(m, 2H), 1.94(m, 2H), 3.39(t, 2H), 4.00(t, 3H), 6.98(d, 2H), 7.53(d, 2H) |
| 64 | C$_4$H$_9$O—C$_6$H$_4$— | —CH$_3$ | recrystallization from 2-propanol | white solid, 52–53/ 0.99(t, 3H), 1.51(m, 2H), 1.79(m, 2H), 3.26(s, 3H), 4.03(t, 2H), 6.98(d, 2H), 7.53(d, 2H) |
| 65 | C$_4$H$_9$O—C$_6$H$_4$— | —C$_3$H$_7$ | chromatography (hexane:ethyl acetate = 5:1) | pale yellow liquid/ 0.98(t, 3H), 1.10(t, 3H), 1.49(m, 2H), 1.78(m, 2H), 1.92(m, 2H), 3.38(t, 2H), 4.02(t, 2H), 6.98(d, 2H), 7.52(d, 2H) |

TABLE 2-continued $$R_A-\underset{F_3C}{\overset{}{C}}=N-O-\underset{\underset{O}{\overset{O}{\|}}}{\overset{\overset{O}{\|}}{S}}-R_B$$

| Ex. | R_A | R_B | Purification | State: mp(° C.)/ ¹H-NMR [δ(ppm)] |
|---|---|---|---|---|
| 66 | 2,3-dihydro-1,4-benzodioxin-6-yl (methyl-substituted) | —C₃H₇ | recrystallization with ethanol | white solid, 98/1.11(t, 3H), 1.92(m, 2H), 3.39(t, 2H), 4.32(m, 4H), 6.97(d, 1H), 7.05(m, 2H) |
| 67 | 2-methylthien-5-yl | —C₃H₇ | chromatography (hexane:ethyl acetate = 5:1) | yellow liquid/1.12(t, 3H), 1.98(m, 2H), 3.45(t, 2H), 7.22–7.27(m, 1H), 7.77–7.85(m, 2H) |
| 68 | 4-(C₁₂H₂₅O)-3-isopropylphenyl (methyl-substituted) | —C₃H₇ | chromatography (hexane:ethyl acetate = 20:1) | yellow liquid/0.88(t, 3H), 1.12(t, 3H), 1.18–1.43(m, 22H), 1.44–1.53(m, 2H), 1.83(m, 2H), 1.95(m, 2H), 3.28–3.42(m, 3H), 4.01(t, 2H), 6.84–6.90(m, 1H), 7.38–7.42(m, 2H) |
| 69 | 4-(CH₃S(O))-phenyl | —C₃H₇ | chromatography (hexane:ethyl acetate = 3:1) | colorless liquid/1.17(t, 3H), 1.92(m, 2H), 2.80(s, 3H), 3.42(t, 2H), 7.65(d, 2H), 7.78(d, 2H) |
| 70 | 4-(C₂H₅OC(O)(CH₂)₂O)-phenyl | —C₃H₇ | chromatography (hexane:ethyl acetate = 3:1) | colorless liquid/1.10(t, 3H), 1.27(t,3H), 1.92(m, 2H), 2.82(t, 2H), 3.39(t, 2H), 4.20(q, 2H), 4.30(m, 4H), 7.02(d, 2H), 7.51(d, 2H) |
| 71 | 4-(C₁₈H₃₃O)-3-methylphenyl (methyl-substituted) | —C₃H₇ | chromatography (hexane:ethyl acetate = 13:1) | white solid, 38–40/ 0.88(t, 3H), 1.10(t, 3H), 1.22–1.42(m, 24H), 1.42–1.53(m, 2H), 1.78–1.86(m, 2H), 1.88–1.98(m, 2H), 2.25(s, 3H), 3.38(t, 2H), 4.02(t, 2H), 6.88(d, 1H), 7.32(s, 1H), 7.40(d, 1H) |
| 72 | 4-(C₁₂H₂₅O)-3-methylphenyl (methyl-substituted) | —C₃H₇ | chromatography (methylene chloride) | pale yellow liquid/ 0.89(t, 3H), 1.12(t, 3H), 1.20–1.41(m, 16H), 1.42–1.53(m, 2H), 1.83(m, 2H), 1.94(m, 2H), 2.24(s, 3H), 3.40(t, 2H), 4.01(t, 2H), 6.87(d, 1H), 7.33(s, 1H), 7.40(d, 1H) |
| 73 | 4-(C₃H₇S(O)₂O)-phenyl (methyl-substituted) | —C₃H₇ | recrystallization from ethanol | white solid, 73–74/ 1.08–1.18(m, 6H), 1.94(m, 2H), 2.07(m, 2H), 3.32(t, 2H), 3.40(t, 2H), 6.94(d, 2H), 7.57(d, 2H) |
| 74 | 4-(N,N-dimethylamino)phenyl (methyl-substituted) | —C₃H₇ | chromatography (hexane:ethyl acetate = 3:1) | yellow solid, 105/ 1.08(t, 3H), 1.90(m, 2H), 3.04(s, 6H), 3.38(t, 2H), 6.69(d, 2H), 7.58(d, 2H) |

EXAMPLE 75

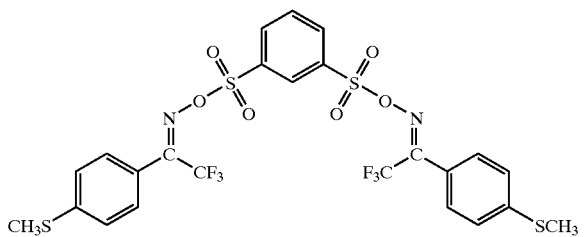

Compound of formula III, R₁ is

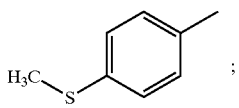

R₂ is F; R₃' is

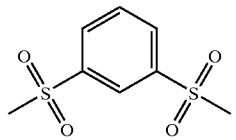

The compound of example 75 is prepared by reacting 2 moles of the corresponding oxime with one mole of the corresponding dichloride according to the method described in example 1.2. The compound is purified by recrystallization from toluene and is a white solid with a melting point of 135–137° C. ¹H-NMR data, δ [ppm]: 2.53 (s, 6H), 7.32 (d, 4H), 7.39 (d, 4H), 7.39 (d, 4H), 7.88 (t, 1H), 8.36 (d, 2H), 8.63 (s, 1H).

EXAMPLE 76

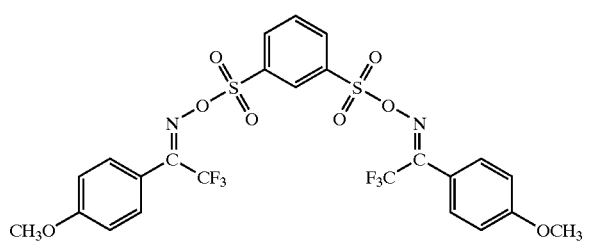

Compound of formula III, R₁ is

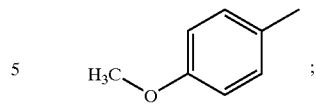

R₂ is F; R₃' is

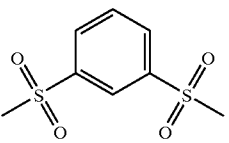

The compound of example 76 is prepared by reacting 2 moles of the corresponding oxime with one mole of the corresponding dichloride according to the method described in example 1.2. The compound is purified by recrystallization from ethanol and is a white solid with a melting point of 127–128° C. ¹H-NMR data, δ [ppm]: 3.88 (s, 6H), 6.98 (d, 4H), 7.47 (d, 4H), 7.87 (t, 1H), 8.35 (d, 2H), 8.62 (s, 1H).

EXAMPLE 77

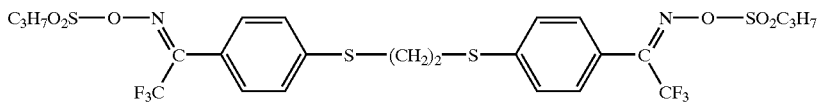

Compound of formula II; R₁' is

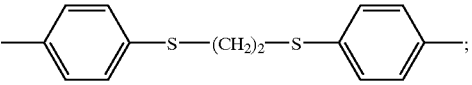

R₂ is F; R₃ is —SO₂C₃H₇

The compound of example 77 is prepared by reacting 1 mole of the corresponding bisoxime with 2 moles of the corresponding chloride according to the method described in example 1.2. The compound is isolated by recrystallization from methanol and is a white solid with a melting point of 84–86° C. ¹H-NMR data (CDCl₃); δ [ppm]: 1.11 (t, 6H), 1.93 (m, 4H), 3.24 (s, 4H), 3.40 (t, 4H), 7.37 (d, 4H), 7.44 (d, 4H).

EXAMPLE 78

2,2,2-Trifluoro-1-(4-methoxyphenyl)-ethanone oxime-O-(1-propylsulfonate) (Mixture of E-, Z-isomers)

78.1: 2,2,2-Trifluoro-1-(4-methoxyphenyl)-ethanone oxime (mixture of E-, Z-isomers)

10 g (49.0 mmol) of 2,2,2-trifluoro-1-(4-methoxyphenyl)-ethanone are dissolved in 100 ml of ethanol. To the solution are added 4.1 g (58.8 mmol) of hydroxylammonium chloride and 11.9 ml (147 mmol) of pyridine. The reaction mixture is refluxed for 4 hours, and the solvent is distilled off by a rotary evaporator. The residue is poured into 50 ml of water, and extracted with 100 ml and 50 ml of ethyl acetate. The organic phase is washed with potassium hydrogen sulfate aqueous solution, water, and brine, dried over MgSO$_4$, and concentrated. The residue is purified by chromatography with methylene chloride, yielding 5.3 g of 2,2,2-trifluoro-1-(4-methoxyphenyl)-ethanone oxime as a white solid with a melting point of 62–80° C. The structure is confirmed by the $^1$H-NMR spectrum (CDCl$_3$). δ [ppm]: 3.84 (s, 3H), 6.93(E)/6.99(Z) (d, 2H), 7.45(E)/7.55(Z) (d, 2H), 8.78 (br s, 1H). The signals are tentatively assigned to the E- and Z-conformations. The spectrum indicates the compound is a mixture of E- and Z-isomers. The ratio of the mixture is estimated to be E:Z=1:1.

78.2: 2,2,2-Trifluoro-1-(4-methoxyphenyl)-ethanone oxime-O-(1-propylsulfonate) (mixture of E-, Z-isomers)

3.7 g (17.0 mmol) of 2,2,2-trifluoro-1-(4-methoxyphenyl)-ethanone oxime (mixture of isomers) are dissolved in 20 ml of THF and cooled in an ice bath. To the solution are added 2.7 g (18.7 mmol) of 1-propanesulfonyl chloride, followed by dropwise addition of 3.6 ml (25.5 mmol) of triethylamine. The reaction mixture is stirred at 0° C. for 1 hour, poured into ice water, and extracted with ethyl acetate. The organic phase is washed with water and brine, dried over MgSO$_4$, and concentrated. The residue is purified by chromatography with methylene chloride, yielding 5.4 g (16.5 mmol; 97%) of 2,2,2-trifluoro-1-(4-methoxyphenyl)-ethanone oxime-O-(1-propylsulfonate) as a pale yellow liquid. The structure is confirmed by the $^1$H-NMR spectrum (CDCl$_3$). δ [ppm]: 1.11 (t, 3H), 1.88–2.02 (m, 2H), 3.34–3.43 (m, 2H), 3.88 (s, 3H), 6.95–7.03 (m, 2H), 7.52–7.58 (m, 2H). The spectrum indicates the compound is a mixture of E- and Z-isomers.

EXAMPLE 79

2,2,2-Trifluoro-1-(4-methoxyphenyl)-ethanone oxime-O-(1-propylsulfonate) (Single Isomer)

79.1: 2,2,2-Trifluoro-1-(4-methoxyphenyl)-ethanone oxime (Single Isomer)

118.5 g (0.58 mol) of 2,2,2-trifluoro-1-(4-methoxyphenyl)-ethanone are dissolved in 470 ml of ethanol and heated at 80° C. To the solution are added 42.4 g (0.61 mol) of hydroxylammonium chloride and 80.9 g (0.99 mol) of sodium acetate dissolved in 240 ml of water. The reaction mixture is refluxed for 5 hours, and the solvent is distilled off by a rotary evaporator. The residue is poured into 500 ml of water, and a white solid is precipitated. The solid is isolated by filtration and rinsed with water, and purified by recrystallization from toluene, yielding 73.1 g of 2,2,2-trifluoro-1-(4-methoxyphenyl)-ethanone oxime as a white solid. The structure is confirmed by the $^1$H-NMR spectrum (CDCl$_3$). δ [ppm]: 3.84 (s, 3H), 6.99 (d, 2H), 7.55 (d, 2H), 9.11 (br s, 1H). The spectrum indicates the compound is a single isomer, which is tentatively assigned as Z-conformation.

79.2: 2,2,2-Trifluoro-1-(4-methoxyphenyl)-ethanone oxime-O-(1-propylsulfonate) (Single Isomer)

12.0 g (54.8 mmol) of 2,2,2-trifluoro-1-(4-methoxyphenyl)-ethanone oxime (single isomer) are dissolved in 100 ml of THF and cooled in an ice bath. To the solution are added 9.4 g (65.7 mmol) of 1-propanesulfonyl chloride, followed by dropwise addition of 8.3 g (82.1 mmol) of triethylamine. The reaction mixture is stirred at 0° C. for 1 hour, poured into ice water, and extracted with ethyl acetate. The organic phase is washed with water and brine, dried over MgSO$_4$, and concentrated. The residue is purified by chromatography with methylene chloride, yielding 15.8 g (48.6 mmol; 89%) of 2,2,2-trifluoro-1-(4-methoxyphenyl)-ethanone oxime-O-(1-propylsulfonate) as a pale yellow liquid. The structure is confirmed by the $^1$H-NMR spectrum (CDCl$_3$). δ [ppm]: 1.11 (t, 3H), 1.94 (m, 2H), 3.39 (t, 2H), 3.88 (s, 3H), 7.00 (d, 2H), 7.54 (d, 2H). The spectrum indicates that the compound is a single isomer, which is tentatively assigned as Z-conformation.

EXAMPLE 80

2,2,2-Trifluoro-1-(4-phenoxyphenyl)-ethanone oxime-O-(1-propylsulfonate) (Mixture of E-, Z-isomers)

80.1: 2,2,2-Trifluoro-1-(4-phenoxyphenyl)-ethanone oxime (mixture of E-, Z-isomers)

122 g (0.46 mol) of 2,2,2-trifluoro-1-(4-phenoxyphenyl)-ethanone are dissolved in 370 ml of ethanol and heated at 80° C. To the solution are added 33.3 g (0.48 mol) of hydroxylammonium chloride and 63.7 g (0.78 mol) of sodium acetate dissolved in 190 ml of water. The reaction mixture is refluxed for 5.5 hours, and poured into water. A pale yellow solid is precipitated. The solid is isolated by filtration and rinsed with water, and added in hexane and heated at 60° C. for 20 min. After cooling, the solid is isolated and rinsed with hexane, yielding 109 g of 2,2,2-trifluoro-1-(4-phenoxyphenyl)-ethanone oxime as a white solid. The structure is confirmed by the $^1$H-NMR spectrum (CDCl$_3$). δ [ppm]: 7.00–7.10 (m, 4H), 7.18 (t, 1H), 7.39 (t, 2H), 7.55 (d, 2H), 9.35 (br s, 1H).

80.2: 2,2,2-Trifluoro-1-(4-phenoxyphenyl)-ethanone oxime-O-(1-propylsulfonate) (Mixture of E-, Z-isomers)

10 g (35.6 mmol) of 2,2,2-trifluoro-1-(4-phenoxyphenyl)-ethanone oxime (mixture of isomers) are dissolved in 70 ml of THF and cooled in an ice bath. To the solution are added 7.2 g (50.2 mmol) of 1-propanesulfonyl chloride, followed by dropwise addition of 6.3 g (62.7 mmol) of triethylamine. The reaction mixture is stirred at 0° C. for 1 hour, poured into ice water, and extracted with ethyl acetate. The organic phase is washed with water and brine, dried over MgSO$_4$, and concentrated. The residue is purified by chromatography with hexane/ethyl acetate (5:1), yielding 8.0 g (20.7 mmol; 58%) of 2,2,2-trifluoro-1-(4-phenoxyphenyl)-ethanone oxime-O-(1-propylsulfonate) as a white solid with melting point of 48–53° C. The structure is confirmed by the $^1$H-NMR spectrum (CDCl$_3$). δ [ppm]: 1.07–1.18 (m, 3H), 1.92(Z)/2.10(E) (m, 2H), 3.40(Z)/3.67(E) (t, 2H), 7.00–7.12 (m, 4H), 7.15–7.28 (m, 1H), 7.34–7.45 (m, 2H), 7.51 (d, 2H). The signals are tentatively assigned to the E- and Z-conformations. The spectrum indicates the compound is a mixture of E- and Z-isomers. The ratio of the mixture is estimated to be E:Z=1:5.

EXAMPLE 81

2,2,2-Trifluoro-1-(4-phenoxyphenyl)-ethanone oxime-O-(1-propylsulfonate) (Single Isomer)

81.1: 2,2,2-Trifluoro-1-(4-phenoxyphenyl)-ethanone oxime (Single Isomer)

35 g (124 mmol) of 2,2,2-trifluoro-1-(4-phenoxyphenyl)-ethanone oxime (mixture of E- and Z-isomers) prepared according to the method described in example 80.1 is dissolved in 300 ml of methylene chloride. To the solution is added 1.1 ml of conc. HCl and stirred at room temperature for 4.5 hours. The reaction mixture is washed with water and brine, dried over MgSO$_4$, and concentrated, yielding 33.4 g of 2,2,2-trifluoro-1-(4-methoxyphenyl)-ethanone oxime (single isomer) as a white solid. The structure is confirmed by the $^1$H-NMR spectrum (CDCl$_3$). δ [ppm]: 7.00–7.12 (m, 4H), 7.19 (t, 1H), 7.39 (t, 2H), 7.57 (d, 2H), 8.95 (s, 1H).

81.2: 2,2,2-Trifluoro-1-(4-phenoxyphenyl)-ethanone oxime-O-(1-propylsulfonate) (Single Isomer)

10.0 g (35.6 mmol) of 2,2,2-trifluoro-1-(4-phenoxyphenyl)-ethanone oxime (single isomer) are dissolved in 80 ml of THF and cooled in an ice bath. To the solution are added 5.6 g (39.1 mmol) of 1-propanesulfonyl chloride, followed by dropwise addition of 5.4 g (53.3 mmol) of triethylamine. The reaction mixture is stirred at 0° C. for 1 hour, poured into ice water, and extracted with ethyl acetate. The organic phase is washed with water and brine, dried over $MgSO_4$, and concentrated. The residue is purified by recrystallization from hexane, yielding 12.6 g (32.5 mmol; 91%) of 2,2,2-trifluoro-1-(4-phenoxyphenyl)-ethanone oxime-O-(1-propylsulfonate) as a white solid with a melting point of 63–64° C. The structure is confirmed by the $^1$H-NMR spectrum ($CDCl_3$). δ [ppm]: 1.11 (t, 3H), 1.92 (m, 2H), 3.40 (t, 2H), 7.05 (d, 2H), 7.11 (d, 2H), 7.23 (t, 1H), 7.42 (t, 2H), 7.51 (d, 2H). The spectrum the compound is a single isomer, which is tentatively assigned as Z-conformation.

EXAMPLE 82

2,2,2-Trifluoro-1-(4-dodecyloxyphenyl)-ethanone oxime-O-(1-propylsulfonate) (Mixture of E-, Z-isomers)

82.1: 2,2,2-Trifluoro-1-(4-dodecyloxyphenyl)-ethanone oxime (mixture of E-, Z-isomers)

32 g (89.3 mmol) of 2,2,2-trifluoro-1-(4-dodecyloxyphenyl)-ethanone are dissolved in 200 ml of ethanol. To the solution are added 7.4 g (107 mmol) of hydroxylammonium chloride and 21.2 g (268 mmol) of pyridine. The reaction mixture is refluxed for 1.5 hours, and the solvent is distilled off by a rotary evaporator. The residue is poured into water, and extracted with ethyl acetate. The organic phase is washed with potassium hydrogen sulfate aqueous solution, water, and brine, dried over $MgSO_4$, and concentrated. The residue is purified by recrystallization from hexane/toluene, yielding 8.4 g of 2,2,2-trifluoro-1-(4-dodecyloxyphenyl)-ethanone oxime as a white solid with a melting point of 70–72° C. The structure is confirmed by the $^1$H-NMR spectrum ($CDCl_3$). δ [ppm]: 0.89 (t, 3H), 1.20–1.40 (m, 16H), 1.40–1.50 (m, 2H), 1.79 (m, 2H), 3.86–4.03 (m, 2H), 6.93(E)/6.97(Z) (d, 2H), 7.44(E)/7.53(Z) (d, 2H), 8.59(Z)/8.61 (E) (br s, 1H). The signals are tentatively assigned to the E- and Z-conformations. The spectrum indicates that the compound is a mixture of E- and Z-isomers. The ratio of the mixture is estimated to be E:Z=1:4.

82.2: 2,2,2-Trifluoro-1-(4-dodecyloxyphenyl)-ethanone oxime-O-(1-propylsulfonate) (Mixture of E-, Z-isomers)

8.0 g (21.4 mmol) of 2,2,2-trifluoro-1-(4-dodecyloxyphenyl)-ethanone oxime (mixture of E-, Z-isomers) are dissolved in 50 ml of THF and cooled in an ice bath. To the solution are added 3.4 g (23.6 mmol) of 1-propanesulfonyl chloride, followed by dropwise addition of 3.3 g (32.1 mmol) of triethylamine. The reaction mixture is stirred at 0° C. for 1 hour, poured into ice water, and extracted with ethyl acetate. The organic phase is washed with water and brine, dried over $MgSO_4$, and concentrated. The residue is purified by recrystallization from methanol, yielding 9.1 g (19.0 mmol; 89%) of 2,2,2-trifluoro-1-(4-dodecyloxyphenyl)-ethanone oxime-O-(1-propylsulfonate) as a white solid with a melting point of 40–41° C. The structure is confirmed by the $^1$H-NMR spectrum ($CDCl_3$). δ [ppm]: 0.88 (t, 3H), 1.10 (t, 3H), 1.20–1.40 (m, 16H), 1.40–1.50 (m, 2H), 1.75–1.85 (m, 2H), 1.87–1.98 (m, 2H), 3.32–3.42 (m, 2H), 4.00 (t, 2H), 6.93–7.00 (m, 2H), 7.48–7.57 (m, 2H). The spectrum indicates that the compound is a mixture of E- and Z-isomers.

EXAMPLE 83

2,2,2-Trifluoro-1-(4-dodecyloxyphenyl)-ethanone oxime-O-(1-propylsulfonate) (Single Isomer)

83.1: 2,2,2-Trifluoro-1-(4-dodecyloxyphenyl)-ethanone oxime (Single Isomer)

15 g (41.8 mmol) of 2,2,2-trifluoro-1-(4-dodecyloxyphenyl)-ethanone are dissolved in 100 ml of ethanol. To the solution are added 3.5 g (50.2 mmol) of hydroxylammonium chloride and 10.1 ml (125.4 mmol) of pyridine. The reaction mixture is refluxed for two hours, and the solvent is distilled off by a rotary evaporator. The residue is poured into 100 ml of water, and extracted with 100 ml and then with 50 ml of ethyl acetate. The organic phase is washed with potassium hydrogen sulfate aqueous solution, water, and brine, dried over $MgSO_4$, and concentrated. The residue is dissolved in 100 ml of methylene chloride. To the solution is added 4.2 g of conc. HCl. The reaction mixture is stirred at room temperature overnight, and poured into water. After the aqueous phase is removed, the organic phase is washed with water and brine, dried over $MgSO_4$, and concentrated. The residue is purified by recrystallization from hexane, yielding 9.7 g of 2,2,2-trifluoro-1-(4-dodecyloxyphenyl)-ethanone oxime as a white solid with a melting point of 75–76° C. The structure is confirmed by the $^1$H-NMR spectrum ($CDCl_3$). δ [ppm]: 0.89(t, 3H), 1.21–1.40 (m, 16H), 1.40–1.52 (m, 2H), 1.80 (m, 2H), 3.99 (t, 2H), 6.97 (d, 2H), 7.53 (d, 2H), 8.43 (s, 1H). The spectrum indicates that the compound is a single isomer, which is tentatively assigned as Z-conformation. When sulfuric acid is used in place of HCl, 2,2,2-trifluoro-1-(4-dodecyloxyphenyl)-ethanone oxime of the single isomer is also obtained.

83.2: 2,2,2-Trifluoro-1-(4-dodecyloxyphenyl)-ethanone oxime-O-(1-propylsulfonate) (Single Isomer)

7.0 g (18.7 mmol) of 2,2,2-trifluoro-1-(4-dodecyloxyphenyl)-ethanone oxime (single isomer) are dissolved in 50 ml of THF and cooled in an ice bath. To the solution are added 2.9 g (20.6 mmol) of 1-propanesulfonyl chloride, followed by dropwise addition of 3.9 ml (28.1 mmol) of triethylamine. The reaction mixture is stirred at 0° C. for 1 hour, poured into ice water, and extracted with ethyl acetate. The organic phase is washed with water and brine, dried over $MgSO_4$, and concentrated. The residue is purified by recrystallization from methanol, yielding 7.6 g (15.9 mmol; 85%) of 2,2,2-trifluoro-1-(4-dodecyloxyphenyl)-ethanone oxime-O-(1-propylsulfonate) as a white solid with a melting point of 42–44° C. The structure is confirmed by the $^1$H-NMR spectrum ($CDCl_3$). δ [ppm]: 0.88 (t, 3H), 1.10 (t, 3H), 1.20–1.40 (m, 16H), 1.40–1.50 (m, 2H), 1.80 (m, 2H), 1.94 (m, 2H), 3.48 (t, 2H), 4.00 (t, 2H), 6.97 (d, 2H), 7.53 (d, 2H). The spectrum indicates that the compound is a single isomer, which is tentatively assigned as Z-conformation.

EXAMPLE 84

2,2,2-Trifluoro-1-(4-hexadecyloxyphenyl)-ethanone oxime-O-(1-propylsulfonate) (Mixture of E-, Z-isomers)

84.1: 2,2,2-Trifluoro-1-(4-hexadecyloxyphenyl)-ethanone oxime (Mixture of E-, Z-isomers)

27 g (65.1 mmol) of 2,2,2-trifluoro-1-(4-hexadecyloxyphenyl)-ethanone are dissolved in 100 ml of ethanol. To the solution are added 4.5 g (65.1 mmol) of hydroxylammonium chloride and 12.9 g (163 mmol) of pyridine. The reaction mixture is refluxed for 4 hours, and the solvent is distilled off by a rotary evaporator. The residue is poured into water, and extracted with ethyl acetate. The organic phase is washed with potassium hydrogen sulfate aqueous solution, water, and brine, dried over MgSO$_4$, and concentrated. The residue is purified by recrystallization from hexane/toluene, yielding 13.5 g of 2,2,2-trifluoro-1-(4-hexadecyloxyphenyl)-ethanone oxime as a beige solid with a melting point of 76–80° C. The structure is confirmed by the $^1$H-NMR spectrum (CDCl$_3$). δ [ppm]: 0.88 (t, 3H), 1.20–1.40 (m, 24H), 1.40–1.50 (m, 2H), 1.75–1.84 (m, 2H), 3.96–4.02 (m, 2H), 6.89(E)/6.95(Z) (d, 2H), 7.43(E)/7.52(Z) (d, 2H), 8.28(Z)/8.43(E) (br s, 1H). The signals are tentatively assigned to the E- and Z-conformations. The spectrum indicates that the compound is a mixture of E- and Z-isomers. The ratio of the mixture is estimated to be E:Z=7:3.

84.2: 2,2,2-Trifluoro-1-(4-hexadecyloxyphenyl)-ethanone oxime-O-(1-propylsulfonate) (Mixture of E-, Z-isomers)

8.0 g (18.6 mmol) of 2,2,2-trifluoro-1-(4-hexadecyloxyphenyl)-ethanone oxime (mixture of E-, Z-isomers) are dissolved in 50 ml of THF and cooled in an ice bath. To the solution are added 2.9 g (20.5 mmol) of 1-propanesulfonyl chloride, followed by dropwise addition of 2.8 g (27.9 mmol) of triethylamine. The reaction mixture is stirred at 0° C. for 1 hour, poured into ice water, and extracted with ethyl acetate. The organic phase is washed with water and brine, dried over MgSO$_4$, and concentrated. The residue is purified by recrystallization from methanol, yielding 8.9 g (16.6 mmol; 89%) of 2,2,2-trifluoro-1-(4-hexadecyloxyphenyl)-ethanone oxime-O-(1-propylsulfonate) as a white solid with a melting point of 56–57° C. The structure is confirmed by the $^1$H-NMR spectrum (CDCl$_3$). δ [ppm]: 0.88 (t, 3H), 1.12 (t, 3H), 1.18–1.40 (m, 24H), 1.40–1.50 (m, 2H), 1.76–1.85 (m, 2H), 1.88–2.02 (m, 2H), 3.32–3.44 (m, 2H), 4.02 (t, 2H), 6.93–7.00 (m, 2H), 7.48–7.56 (m, 2H). The spectrum indicates that the compound is a mixture of E- and Z-isomers.

EXAMPLE 85

2,2,2-Trifluoro-1-(4-hexadecyloxyphenyl)-ethanone oxime-O-(1-propylsulfonate) (Single Isomer)

85.1: 2,2,2-Trifluoro-1-(4-hexadecyloxyphenyl)-ethanone oxime (Single Isomer)

5.3 g (12.3 mmol) of 2,2,2-trifluoro-1-(4-hexadecyloxyphenyl)-ethanone oxime (mixture of E- and Z-isomers) prepared according to the method described in example 84.1 are dissolved in 100 ml of methylene chloride. To the solution is added 1.0 ml of conc. HCl and stirred at room temperature overnight. The reaction mixture is washed with water and brine, dried over MgSO$_4$, and concentrated, yielding 5.3 g of 2,2,2-trifluoro-1-(4-hexadecyloxyphenyl)-ethanone oxime (single isomer) as a white solid with a melting point of 84–85° C. The structure is confirmed by the $^1$H-NMR spectrum (CDCl$_3$). δ [ppm]: 0.88 (t, 3H), 1.20–1.40 (m, 24H), 1.40–1.50 (m, 2H), 1.80 (m, 2H), 4.00 (t, 2H), 6.95 (d, 2H), 7.52 (d, 2H), 8.06 (s, 1H). The spectrum indicates that the compound is a single isomer, which is tentatively assigned as Z-conformation.

85.2: 2,2,2-Trifluoro-1-(4-hexadecyloxyphenyl)-ethanone oxime-O-(1-propylsulfonate) (Single Isomer)

5.2 g (12.2 mmol) of 2,2,2-trifluoro-1-(4-hexadecyloxyphenyl)-ethanone oxime (single isomer) are dissolved in 50 ml of THF and cooled in an ice bath. To the solution are added 1.9 g (13.3 mmol) of 1-propanesulfonyl chloride, followed by dropwise addition of 1.84 g (18.2 mmol) of triethylamine. The reaction mixture is stirred at 0° C. for 1 hour, poured into ice water, and extracted with ethyl acetate. The organic phase is washed with water and brine, dried over MgSO$_4$, and concentrated. The residue is purified by recrystallization from methanol, yielding 5.8 g (10.8 mmol; 89%) of 2,2,2-trifluoro-1-(4-hexadecyloxyphenyl)-ethanone oxime-O-(1-propylsulfonate) as a white solid with a melting point of 59–60° C. The structure is confirmed by the $^1$H-NMR spectrum (CDCl$_3$). δ [ppm]: 0.88 (t, 3H), 1.12 (t, 3H), 1.23–1.41 (m, 24H), 1.41–1.50 (m, 2H), 1.80 (m, 2H), 1.93 (m, 2H), 3.40 (t, 2H), 4.02 (t, 2H), 6.97 (d, 2H), 7.53 (d, 2H). The spectrum indicates that the compound is a single isomer, which is tentatively assigned as Z-conformation.

EXAMPLE 86

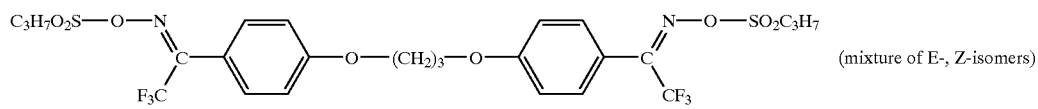

(mixture of E-, Z-isomers)

Compound of formula II; RA$_1$' is

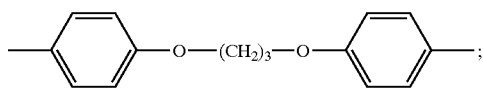

R$_2$ is F; R$_3$ is —SO$_2$C$_3$H$_7$ 86.1:

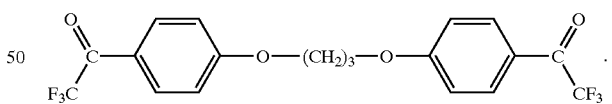

The compound of example 86.1 is prepared by reacting one mole 1,3-diphenoxypropane with 2 moles of 4-dimethylaminopyridine, 2 moles of trifluoroacetic anhydride, and 5 moles of AlCl$_3$ according to the method described in example 7.1. The crude product is purified by recrystallization from toluene.

86.2:

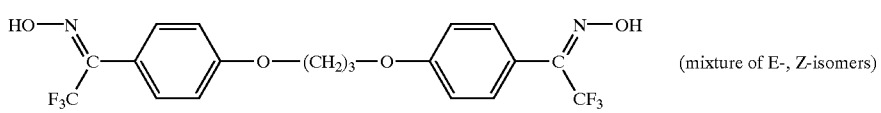

(mixture of E-, Z-isomers)

18.0 g (42.8 mmol) of the compound of example 86.1 are dissolved in 100 ml of ethanol. To the solution are added 6.0 g (85.7 mmol) of hydroxylammonium chloride and 16.9 g (214 mmol) of pyridine. The reaction mixture is refluxed for 4 hours, and the solvent is distilled off by a rotary evaporator. The residue is poured into water, and extracted with ethyl acetate. The organic phase is washed with potassium hydrogen sulfate aqueous solution, water, and brine, dried over MgSO$_4$, and concentrated. The residue is purified by recrystallization from toluene, yielding 16.1 g of the compound of example 86.2 as a white solid. The structure is confirmed by the $^1$H-NMR spectrum (DMSO-d$_6$). δ [ppm]: 2.22–2.34 (m, 2H), 4.22–4.32 (m, 4H), 7.06–7.17 (m, 4H), 7.47/7.52 (d, 4H). The spectrum indicates that the compound is a mixture of E- and Z-isomers.

86.3:

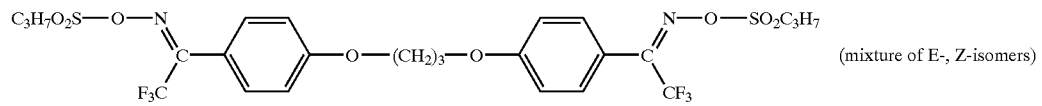

(mixture of E-, Z-isomers)

8.0 g (17.8 mmol) of the compound of example 86.2 (mixture of E-, Z-isomers) are dissolved in 80 ml of THF and cooled in an ice bath. To the solution are added 5.6 g (39.1 mmol) of 1-propanesulfonyl chloride, followed by dropwise addition of 5.4 g (53.3 mmol) of triethylamine. The reaction mixture is stirred for 2 hours at 0° C., poured into ice water, and extracted with ethyl acetate. The organic phase is washed with water and brine, dried over MgSO$_4$, and concentrated. The residue is purified by chromatography with hexane/ethyl acetate (2:1), yielding 10.7 g (16.1 mmol; 91%) of the compound of example 86.3 as a pale yellow solid with a melting point of 80–84° C. The structure is confirmed by the $^1$H-NMR spectrum (CDCl$_3$). δ [ppm]: 1.12 (t, 6H), 1.97 (m, 4H), 2.36 (m, 2H), 3.35–3.45 (m, 4H), 4.25 (t, 4H), 6.98–7.06 (m, 4H), 7.54/7.58 (d, 4H). The spectrum indicates that the compound is a mixture of E- and Z-isomers.

EXAMPLE 87

21.0 g (50.0 mmol) of example 86.1 are dissolved in 150 ml of ethanol. To the solution are added 8.4 g (120 mmol) of hydroxylammonium chloride and 23.8 g (300 mmol) of pyridine. The reaction mixture is refluxed for 1.5 hours, and the solvent is distilled off by a rotary evaporator. The residue is poured into water, and extracted with ethyl acetate. The organic phase is washed with potassium hydrogen sulfate aqueous solution, water, and brine, dried over MgSO$_4$, and concentrated. The residue is dissolved in 150 ml of ethyl acetate. To the solution is added 0.43 ml of conc. HCl and stirred at room temperature for 2 hours. The reaction mixture is washed with water and brine, dried over MgSO$_4$, and concentrated. The residue is purified by recrystallization from toluene, yielding 21.4 g of the compound of example 87.1 as a white solid. The structure is confirmed by the $^1$H-NMR spectrum (DMSO-d$_6$). δ[ppm]: 2.43 (m, 2H), 4.42 (t, 4H), 7.30 (d, 4H), 7.70 (d, 4H). The spectrum indicates that compound is a single isomer, which is tentatively assigned as Z, Z-conformation.

87.2:

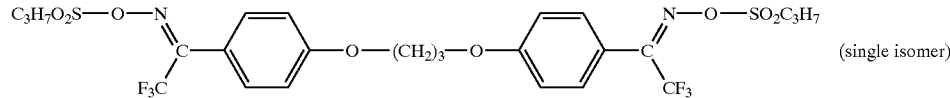

(single isomer)

8.0 g (17.8 mmol) of the compound of example 87.1 (single isomer) are dissolved in 80 ml of THF and cooled in an ice bath. To the solution are added 5.6 g (39.1 mmol) of 1-propanesulfonyl chloride, followed by dropwise addition of 5.4 g (53.3 mmol) of triethylamine. The reaction mixture is stirred for 2 hours at 0° C., poured into ice water, and extracted with ethyl acetate. The organic phase is washed with water and brine, dried over MgSO$_4$, and concentrated. The residue is purified by recrystallization from methanol, yielding 9.1 g (13.7 mmol; 77%) of the compound of example 87.2 as a white solid with a melting point of 60–62° C. The structure is confirmed by the $^1$H-NMR spectrum 87.1:

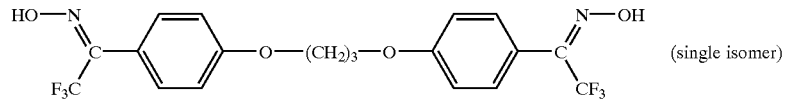

(single isomer)

(CDCl$_3$). δ [ppm]: 1.12 (t, 6H), 1.97 (m, 4H), 2.36 (m, 2H), 3.39 (t, 4H), 4.25 (t, 4H), 7.02 (d, 4H), 7.53 (d, 4H). The spectrum indicates that the compound is a single isomer, which is tentatively assigned as Z, Z-conformation.

EXAMPLE 88

A chemically amplified positive resist formulation is prepared by mixing the following components:

- 100.0 parts of a resin binder (a copolymer of 22 mol-% of styrene, 69 mol-% of p-hydroxy-styrene and 9 mol-% of t-butyl acrylate, having a Mw of 9850; $^{RTM}$Maruzen MARUKA LYNCUR PHS/STY/TBA, provided by Maruzen Oil Company, Japan)
- 0.4 parts of a leveling agent (FC-430, provided by 3M)
- 400.0 parts of propylene glycol methyl ether acetate (PGMEA) (provided by Tokyo Kasei, Japan)
- 4.0 parts of the photoacid generator to be tested The resist formulation is spin coated onto a hexamethyl dimethylsilane-treated silicone wafer at 6500 rpm for 60 seconds and softbaked for 90 seconds at 140° C. on a hotplate to obtain a film thickness of 800 nm. The resist film is then exposed to 254 nm deep UV exposure wavelength through a narrow band interference filter and a multidensity quartz mask using an Ushio's high pressure mercury lamp, UXM-501MD, and a mask aligner Canon PLA-521 and then post exposure baked for 90 seconds at 140° C. on a hotplate and then developed. The exposure intensity is measured with Unimeter UIT-150 from Ushio. The dose to clear (E$_0$), which is the dose just sufficient to completely remove the resist film with 90 seconds immersion development in 2.38% aqueous tetramethyl ammonium hydroxide developer is determined from the measured contrast curve (characteristic curve) as described in: R. Dammel, Diazonaphthoquinone-based Resists, SPIE Tutorial Text Series Vol. TT 11, Optical Engineering Press, p. 10–11 (1993). The smaller the required dose the more sensitive is the resist formulation. The results are collected in table 3 and demonstrate that the compositions are suitable for the preparation of positive photoresists.

TABLE 3

| Compound of example | Dose to Clear (E$_0$) (mJ/(cm$^2$) |
|---|---|
| 2 | 0.18 |
| 3 | 0.18 |
| 5 | 0.10 |
| 6 | 0.23 |
| 13 | 1.14 |
| 16 | 0.19 |
| 17 | 0.24 |
| 20 | 0.16 |
| 21 | 0.16 |
| 26 | 0.25 |
| 27 | 0.15 |
| 29 | 0.07 |

EXAMPLE 89

A chemically amplified negative resist formulation is prepared by mixing the following components:

- 100.0 parts of a resin binder (a poly(p-hydroxystyrene) having a Mw of 11900; $^{RTM}$VP-8000, provided by Nisso, Japan)
- 10.0 parts of a melamine urea resin as cross linker (N,N'-dimethoxymethylurea, $^{RTM}$MX-290, provided by Sanwa Chemical Co., LTD)
- 0.5 parts of a levelling agent ($^{RTM}$FC-430, provided by 3M)
- 7.7 parts of the photoacid generator (PAG) to be tested
- 500.0 parts of propylene glycol methyl ether acetate (PGMEA) (provided by Tokyo Kasei, Japan)

The resist formulation is spin coated onto a hexamethyl dimethylsilane-treated silicone wafer at 6000 rpm for 60 seconds at a thickness of 800 nm. After softbaking for 60 seconds at 110° C. on a vacuum hot plate, a tack-free resist film is obtained. The resist film is then exposed to 254 nm exposure wavelength through a narrow band filter and a multidensity quartz mask using an Ushio's high pressure mercury lamp, UXM-501MD, and a mask aligner Canon PLA-521 in order to determine the Gel Dose (D$_0$) which is obtained analogous to example 88, except that the resist film is baked at 110° C. for 60 seconds after exposure and prior to immersion development for 60 seconds in 2.38% aqueous tetramethyl ammonium hydroxide and gel dose is determined as the dose just sufficient to leave a thin film of crosslinked resist on the substrate after development. Contrast curves (characteristic curves) for both, positive and negative resists are discussed with respect to the dose to clear (for positive resists) and gel dose (with respect to negative resists in: E. Reichmanis and L. F. Thompson, ACS Symp. Ser. 412, Polymers in Microlithography, p. 4–5, American Chemical Society, Washington, D.C. 1989). The obtained negative resist sensitivities are listed in table 4.

TABLE 4

| Compound of example | Gel Dose (D$_0$) (mJ/cm$^2$) |
|---|---|
| 1 | 0.96 |
| 2 | 3.74 |
| 3 | 0.57 |
| 6 | 0.43 |
| 7 | 1.50 |
| 13 | 3.81 |
| 15 | 0.52 |
| 16 | 0.10 |
| 17 | 0.32 |
| 22 | 2.58 |
| 23 | 1.65 |
| 24 | 0.42 |
| 25 | 2.53 |
| 26 | 0.79 |
| 27 | 0.57 |

EXAMPLE 90

A chemically amplified positive resist formulation is prepared by mixing the following components:

- 100.00 parts of the same resin binder as described in Example 88
- 0.48 parts of a leveling agent (FC-430, provided by 3M)
- 475.00 parts of propylene glycol methyl ether acetate (PGMEA) (provided by Tokyo Kasei, Japan)
- 4.0 parts of the photoacid generator to be tested The resist formulation is spin coated onto a hexamethyl dimethylsilane-treated silicone wafer at 3000 rpm for 45 seconds and softbaked for 90 seconds at 140° C. on a hotplate to obtain a film thickness of 800 nm. The resist film is then exposed to deep UV radiation of 254 nm wavelength through a narrow band interference filter and a multidensity quartz mask using an Ushio's high pressure mercury lamp, UXM-501MD, and a mask aligner Canon PLA-521. The samples then are post exposure baked for 90 seconds at 140° C. on a hotplate and developed. The exposure intensity is measured with a Unimeter UIT-150 from Ushio. The Dose to Clear (E$_0$), which is the dose just sufficient to completely remove the resist film with 60 seconds immersion development in 1.79% aqueous tetramethyl ammonium hydroxide developer is determined from the measured contrast curve. The smaller the required dose the more sensitive is the resist formulation. The results are collected in Table 5 and demonstrate that the compositions are suitable for the preparation of positive photoresists.

TABLE 5

| Compound of example | Dose to Clear ($E_0$) [mJ/cm$^2$] |
|---|---|
| 40 | 1.79 |
| 41 | 1.63 |
| 42 | 1.32 |
| 43 | 1.50 |
| 44 | 0.91 |
| 45 | 4.61 |
| 46 | 0.72 |
| 47 | 4.16 |
| 48 | 1.63 |
| 49 | 0.99 |
| 50 | 1.22 |
| 51 | 1.22 |
| 52 | 0.99 |
| 53 | 0.56 |
| 54 | 0.69 |
| 55 | 0.69 |
| 56 | 1.17 |
| 57 | 5.01 |
| 58 | 2.02 |
| 59 | 1.47 |
| 61 | 3.07 |
| 62 | 1.51 |
| 63 | 2.77 |
| 64 | 2.66 |
| 65 | 1.57 |
| 66 | 2.90 |
| 67 | 1.11 |
| 69 | 1.33 |
| 70 | 2.20 |
| 72 | 4.25 |
| 75 | 0.89 |
| 76 | 1.30 |
| 79 | 1.21 |
| 80 | 1.54 |
| 81 | 1.55 |
| 83 | 5.00 |
| 85 | 7.27 |
| 87 | 1.73 |

EXAMPLE 91

The degradation point (Td) of the photolatent acid generator compound in the presence of the same amount (with respect to the weight) of poly(4-hydroxystyrene), which has a Mw of 5100 and is commercially available under the trade name of Maruzene MARUKA LYNCUR PHMC from Maruzene Oil Company of Tokyo, Japan, is determined by DSC analysis (Differential Scanning Calorimetry). The higher the values, the more thermostable are the tested photolatent acid compounds. The results are summarized in the table 6 below.

TABLE 6

| Compound of example | Td (° C.) |
|---|---|
| 1 | >200 |
| 2 | >200 |
| 3 | 180 |
| 5 | 183 |
| 6 | >200 |
| 8 | >200 |
| 13 | 197 |

TABLE 6-continued

| Compound of example | Td (° C.) |
|---|---|
| 15 | 173 |
| 16 | 186 |
| 17 | 192 |
| 18 | 175 |
| 20 | 196 |
| 21 | 176 |
| 22 | 180 |
| 23 | 219 |
| 25 | 197 |
| 27 | 188 |
| 40 | 174 |
| 41 | 170 |
| 42 | >200 |
| 43 | 185 |
| 44 | 186 |
| 45 | 174 |
| 46 | 198 |
| 47 | >200 |
| 48 | >200 |
| 49 | 172 |
| 50 | 193 |
| 51 | >200 |
| 52 | >200 |
| 53 | 186 |
| 54 | 190 |
| 55 | 184 |
| 56 | >200 |
| 57 | >200 |
| 58 | >200 |
| 59 | 191 |
| 61 | >200 |
| 62 | 193 |
| 63 | >200 |
| 64 | >200 |
| 65 | >200 |
| 66 | 186 |
| 67 | 187 |
| 69 | 173 |
| 70 | 175 |
| 72 | >200 |
| 75 | 175 |
| 76 | 175 |
| 79 | 190 |
| 80 | 188 |
| 81 | >200 |
| 83 | >200 |
| 85 | 197 |
| 87 | 188 |

EXAMPLE 91

The degradation point (Td) of the photolatent acid generator compound in the presence of the same amount (with respect to the weight) of poly(4-hydroxystyrene) is measured in the same manner as described in example 91. The results are summarized in table 7 below.

TABLE 7

| Compound of example | Td (° C.) |
|---|---|
| 78 (mixture of isomers) | 116, 185[1] |
| 79 (single isomer of 78) | 190 |
| 80 (mixture of isomers) | 185, >200[1] |
| 81 (single isomer of 80) | >200 |
| 82 (mixture of isomers) | 151, >200[1] |
| 83 (single isomer of 82) | >200 |
| 84 (mixture of isomers) | 150, 197[1] |

TABLE 7-continued

| Compound of example | Td (° C.) |
|---|---|
| 85 (single isomer of 84) | 197 |
| 86 (mixture of isomers) | 140, 188[1)] |
| 87 (single isomer of 86) | 188 |

[1]Two peaks appear in the DSC measurement. The values are estimated from the starting point of the decompositions.

What is claimed is:

1. A compound of the formula Ib, IIb or IIIb

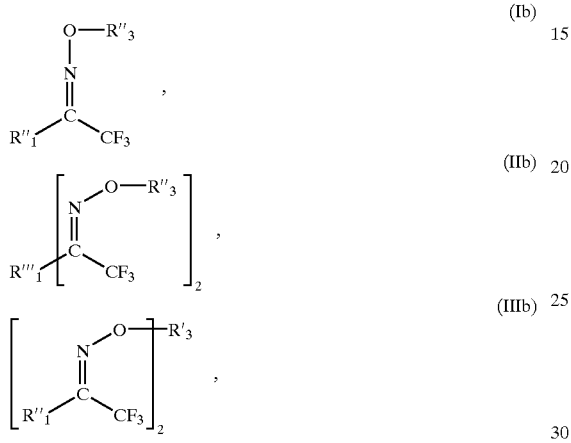

wherein

R"$_1$ is phenyl, which is unsubstituted or substituted by one or more $C_1$–$C_{12}$alkyl, phenyl-$C_1$–$C_3$-alkyl, $C_1$–$C_4$haloalkyl, halogen, phenyl, OR$_4$, NR$_5$R$_6$, SR$_7$, SOR$_7$, and/or SO$_2$R$_7$, optionally the substituents OR$_4$, SR$_7$ and NR$_5$R$_5$ form 5- or 6-membered rings via the radicals R$_4$, R$_5$, R$_6$ and/or R$_7$, with further substituents on the phenyl ring or with one of the carbon atoms of the phenyl ring;

or R"$_1$ is naphthyl, anthracyl or phenanthryl each of which is unsubstituted or substituted by $C_1$–$C_6$alkyl, phenyl, OR$_4$, NR$_5$R$_6$, SR$_7$, SOR$_7$ and/or SO$_2$R$_7$ optionally the substituents OR$_4$, SR$_7$ and NR$_5$R$_6$ form 5- or 6-membered rings via the radicals R$_4$, R$_5$, R$_6$ and/or R$_7$, with further substituents on the phenyl ring or with one of the carbon atoms of the naphthyl, anthracyl or phenanthryl ring or with one of the carbon atoms of the naphthyl, anthracyl or phenanthryl ring;

or R"$_1$ is a heteroaryl radical which is unsubstituted or substituted by $C_1$–$C_6$alkyl, phenyl, OR$_4$, NR$_5$R$_6$, SR$_7$, SOR$_7$, and/or SO$_2$R$_7$, optionally the substituents OR$_4$, SR$_7$ and NR$_5$R$_6$ form 5- or 6-membered rings, via the radicals R$_4$, R$_5$, R$_6$ and/or R$_7$ with further substituents on the heteroaryl ring or with one of the carbon atoms of the heteroaryl ring;

R'''$_1$ is phenylene, naphthylene,

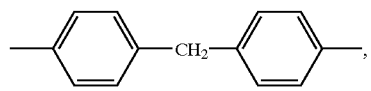

diphenylene or oxydiphenylene, wherein these radicals are unsubstituted or substituted by $C_1$–$C_{12}$alkyl;

or R'''$_1$ is

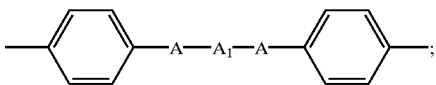

A is —O—, —S—, —NR$_4$—, —O(CO)—, —S(CO)—, —NR$_4$(CO)—, —SO—, —SO$_2$—, or —OSO$_2$—;

A$^1$ is $C_1$–$C_{12}$alkylene or $C_2$–$C_{12}$alkylene, which is interrupted by one or more —O—;

R"$_3$ is $C_1$–$C_{16}$alkylsulfonyl, phenyl-$C_1$–$C_3$alkylsulfonyl, camphorylsulfonyl, naphthylsulfonyl, trimethylphenylsulfonyl; or phenylsulfonyl which is substituted by one or more $C_2$–$C_{16}$alkyl, $C_1$–$C_4$alkoxy, $C_1$–$C_4$haloalkyl and/or halogen; and R'$_3$ is phenylenedisulfonyl, naphthylenedisulfonyl,

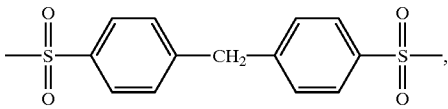

diphenylenedisulfonyl, or oxydiphenylenedisulfonyl, wherein these radicals are unsubstituted or substituted by $C_1$–$C_{12}$alkyl; or R'$_3$ is $C_2$–$C_{12}$alkylenedisulfonyl;

R$_4$ is hydrogen, phenyl, $C_1$–$C_{12}$alkyl which is unsubstituted or substituted by phenyl, OH, $C_1$–$C_{12}$alkoxy, $C_2$–$C_{12}$-alkoxycarbonyl, phenoxy, phenoxycarbonyl, phenylthio, phenylthiocarbonyl, NR$_5$R$_6$, $C_1$–$C_{12}$-alkylsulfonyl, phenylsulfonyl, (4-methylphenyl)sulfonyl and/or by $C_2$–$C_6$alkanoyl;

or R$_4$ is $C_2$–$C_{12}$alkyl which is interrupted by one or more —O—, and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, NR$_5$R$_6$ $C_1$–$C_{12}$alkylsulfonyl, phenylsulfonyl, (4-methylphenyl)sulfonyl and/or by $C_2$–$C_6$alkanoyl;

or R$_4$ is $C_2$–$C_{12}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, NR$_5$R$_6$, $C_1$–$C_{12}$alkylsulfonyl, phenylsulfonyl, (4-methylphenyl)sulfonyl and/or by $C_2$–$C_6$alkanoyl;

or R$_4$ is $C_1$–$C_{12}$ alkylsulfonyl which is unsubstituted or substituted by phenyl, OH, $C_1$–$C_{12}$-alkoxy, $C_2$–$C_{12}$alkoxycarbonyl, phenoxy, phenoxycarbonyl, phenylthio, phenylthiocarbonyl, NR$_5$R$_6$, $C_1$–$C_{12}$alkylsulfonyl, phenylsulfonyl, (4-methylphenyl)sulfonyl and/or by $C_2$–$C_6$alkanoyl;

or R$_4$ is phenylsulfonyl, or (4-methylphenyl)sulfonyl;

R$_5$ and R$_6$ independently of each other are hydrogen or $C_1$–$C_{12}$alkyl which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_1$–$C_6$alkanoyl;

or R$_5$ and R$_6$ are $C_2$–$C_{12}$alkyl which is interrupted by one or more —O—, and which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_1$–$C_6$alkanoyl;

or $R_5$ and $R_6$ are $C_2$–$C_{12}$alkanoyl which is unsubstituted or substituted by phenyl, OH, $C_1$–$C_{12}$-alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or by $C_2$–$C_6$alkanoyl;

or $R_5$ and $R_6$ are $C_1$–$C_{12}$ alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl sulfonyl and/or by $C_2$–$C_6$alkanoyl, or $R_5$ and $R_6$ are phenylsulfonyl, (4-methylphenyl)sulfonyl;

or $R_5$ and $R_6$ are phenyl, benzoyl, naphthylsulfonyl, anthracylsulfonyl or phenanthrylsulfonyl;

or $R_5$ and $R_6$, together with the nitrogen atom to which they are attached, form a 5-, 6- or 7-membered ring which optionally is interrupted by —O— or by —$NR_4$—;

$R_7$ is hydrogen, phenyl, $C_1$–$C_{12}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl and/or by $C_2$–$C_6$alkanoyl, or $R_7$ is $C_2$–$C_{12}$alkyl which is interrupted by one or more —O—, and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl and/or by $C_2$–$C_6$alkanoyl;

or $R_7$ is $C_2$–$C_{12}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl and/or by $C_2$–$C_6$alkanoyl;

or $R_7$ is $C_1$–$C_{12}$ alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_5R_6$, $C_1$–$C_{12}$alkylsulfonyl, phenylsulfonyl, (4-methylphenyl)sulfonyl and/or by $C_2$–$C_6$alkanoyl;

or $R_7$ is phenylsulfonyl, or (4-methylphenyl)sulfonyl; provided that if $R''_1$ is 4-methylphenyl or 4-octylphenyl, then $R''_3$ is not methanesulfonyl.

2. Process for the specific preparation of the thermally stable isomer of the oxime ester compounds of formula Ib, IIb or IIIb according to claim 1, by (1a) treating the isomeric mixture of the corresponding oxime compounds of formula X,

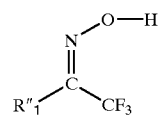

(X)

wherein $R''_1$ is defined as in claim 1, with an acid; and (2a) reacting the thus prepared single isomeric oxime compound with the corresponding acid halides of formula XVI or XVII $R''_3Cl$ (XVI)

$Cl—R'_3—Cl$ (XVII), wherein $R'_3$ and $R''_3$ are as defined in claim 1 or (1b) treating the isomeric mixture of corresponding oxime compound of formula XI

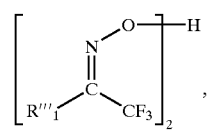

(XI)

wherein $R'''_1$ is defined as in claim 1, with an acid; and (2b) reacting the thus prepared single isomeric oxime compound with the corresponding acid halide of formula XVI $R''_3Cl$ (XVI), wherein $R''_3$ is as defined in claim 1.

3. A composition comprising
(a) a compound which cures upon the action of an acid or a compound whose solubility is increased upon the action of an acid; and
(b) as photosensitive acid donor, at least one compound of the formula Ib, IIb or IIIb according to claim 1.

4. Process for crosslinking compounds that can be crosslinked under the action of an acid, which method comprises adding a compound of formula Ib, IIb and/or IIIb according to claim 1 to the above-mentioned compounds and irradiating imagewise or over the whole area with light having a wavelength of 150–1500 nm.

5. Process according to claim 4 for the preparation of surface coatings, printing inks, printing plates, dental compositions, colour filters, resists, or image-recording materials, or image-recording materials for recording holographic images.

* * * * *